(12) United States Patent
Schetters et al.

(10) Patent No.: US 9,346,862 B2
(45) Date of Patent: May 24, 2016

(54) CANINE BABESIOSIS VACCINE ANTIGEN

(71) Applicant: Intervet Inc., Madison, NJ (US)

(72) Inventors: Theodorus Petrus Maria Schetters, Cujik (NL); Karina Moubri-Menage, Mauguio (FR); Jos Kleuskens, Gennep (NL); Andreas Walter Claudius Rohwer, Worms (DE)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/557,833

(22) Filed: Dec. 2, 2014

(65) Prior Publication Data

US 2015/0079127 A1 Mar. 19, 2015

Related U.S. Application Data

(62) Division of application No. 13/997,805, filed as application No. PCT/EP2011/074120 on Dec. 28, 2011, now abandoned.

(60) Provisional application No. 61/430,298, filed on Jan. 6, 2011.

(30) Foreign Application Priority Data

Dec. 29, 2010 (EP) .................................. 10197303

(51) Int. Cl.
| | | |
|---|---|---|
| *A61K 39/018* | (2006.01) | |
| *C07K 14/44* | (2006.01) | |
| *C07H 21/04* | (2006.01) | |
| *C07K 16/20* | (2006.01) | |
| *A61K 39/00* | (2006.01) | |

(52) U.S. Cl.
CPC .............. *C07K 14/44* (2013.01); *A61K 39/018* (2013.01); *C07H 21/04* (2013.01); *C07K 16/20* (2013.01); *A61K 2039/5156* (2013.01); *A61K 2039/523* (2013.01); *A61K 2039/53* (2013.01); *A61K 2039/552* (2013.01); *A61K 2039/55566* (2013.01); *A61K 2039/55577* (2013.01); *G01N 2333/44* (2013.01)

(58) Field of Classification Search
CPC .............. A61K 2039/5154; A61K 2039/5156; A61K 2039/5256; A61K 2039/54; A61K 2039/552; A61K 2039/55522; A61K 2039/55538; A61K 2039/55561; A61K 2039/55566; A61K 2039/55577; A61K 38/177
See application file for complete search history.

(56) References Cited

U.S. PATENT DOCUMENTS

| | | | |
|---|---|---|---|
| 7,438,912 B2 | 10/2008 | Meinke et al. | |
| 7,700,359 B2 * | 4/2010 | Chan .................... | C12Q 1/6886 435/7.1 |
| 2006/0269541 A1 | 11/2006 | Meinke et al. | |
| 2010/0248390 A1 | 9/2010 | Matsunami et al. | |

FOREIGN PATENT DOCUMENTS

EP 1238983 A1 3/2002

OTHER PUBLICATIONS

Greenspan et al. (Nature Biotechnology, 1999, 7:936-937).*
D7W339, Oct. 5, 2010.
Greenspan et al., Defining epitopes: It's not as easy as it seems, Nature Biotechnology, 1999, 936-937, 17.
Holmes, PSMA specific antibodies and their diagnostic and therapeutic use, PSMA specific antibodies and their diagnostic and therapeutic use, 2001, 511-519, 10(3).
Schetters, et al., Immunity against Babesia rossi infection in dogs vaccinated with antigens from culture supernatants, Science Direct, 2007, pp. 10-19., vol. 144.
Schetters, Vaccine against canine babesiosis, Trends in Parasitology, Apr. 2005, 179-184., vol. 21, No. 4.

* cited by examiner

*Primary Examiner* — Padma V Baskar

(57) ABSTRACT

The present invention relates to the field of veterinary parasitology, especially of canine Babesiosis. In particular the invention relates to a polypeptide being a novel canine *Babesia* antigen (CBA), or fragments thereof, and to compositions comprising this antigen, to nucleic acids encoding the antigen, antibodies against the antigen, and medical uses of this antigen, fragments, antibodies, or encoding nucleic acids. In particular the invention relates to the use of such components in vaccines against canine Babesiosis.

6 Claims, 9 Drawing Sheets

Figure 1

Figure 3:
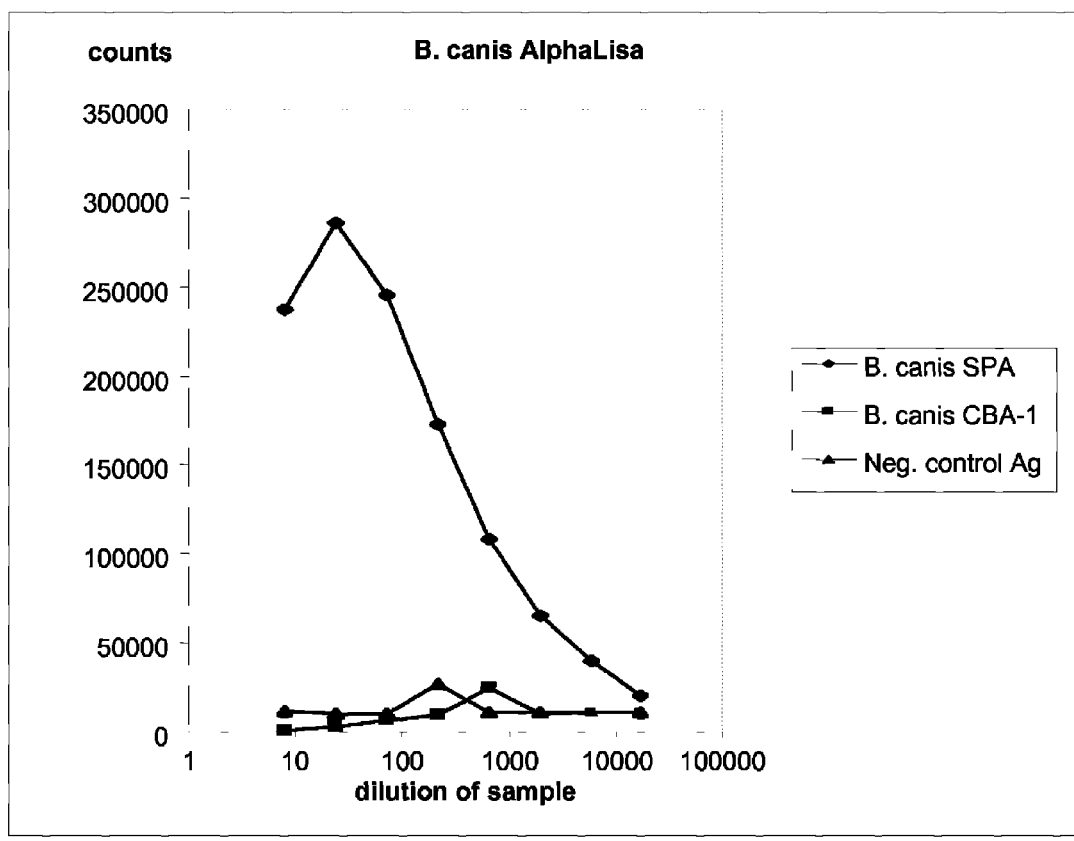

```
CBA-1     1   MMLLFALSTLVTFAFCDGENT  ILLSNVEFHTPVSSVKLLKEY  SSNQESMAV-IMMLTEMP
CBA-2.1   1   MMLLFAFSSLLAVASCTDFNT  MLLSNVSFPQPVSSVKLLEEY  AKYQKGYVLYFQMRDDLP
CBA-2.2   1   MMLLFAFSSLLAVASCTDFNT  MLLSNVSFPQPVSSVKLLEEY  AKDDKVTVI-FSVLDTLP

CBA-1     60  NTSGKLTDGKVHVANDNVKCADLALAYQELKKAGKVTSWSPTDDNDKVVPHGIWFIEGVY
CBA-2.1   61  KKE-DTERFSQYVQLENAECTDLAAIYNIMQREGRIFEYKHESELPD-YPEGLWLLDAQD
CBA-2.2   60  TDEANGTRYSKYKADDNDKCVDLALVFQELQKKGLVKEFGNEDTPPE-EVNGLWLMRGKH

CBA-1     120 ETDKMFEVYKTLTDPEDPSEVTRLT-TVSGASGSAQSQPAGTTDGVSGSAASASGSSGST
CBA-2.1   119 DKEEILHTFETTLPPTSTNGNEHADKTREAPKPRPDAPAASDTQRAQDNQEKTPTESST-
CBA-2.2   119 AGHNMLEVFETLVNP--RRGLEDLPVTPKSAEGRREAVSRS----TAENQAGTNGESGS-

CBA-1     179 TSHSTTATTSSTSTVSTSSSGASTSSSTDQASMLTTQTSYSAGSSVHKSAVVAPTQSTTP
CBA-2.1   178 --------GSRDTVQPQTAPATSNAVTG--TSSTT-------SSVQSQAVIGNSEA--T
CBA-2.2   172 ------S------QTA---SNAGTSQVTAARV---------SGVQAQSVAAGTNG--P

CBA-1     239 DNAESGAKQSKAAVQEPKN--  VLMIITKCDLKAEVTEEQI  RSQGN-PESNGSSSEPTAAS
CBA-2.1   218 TGTQQ-------SAENVK    VLMVLTKCNLKMHVTEEQL  SKHSNIPRKH----------
CBA-2.2   204 QNVREDTVPAPEAVPSNQDMK FLMVLTKCDLMMAIPEEQL  SGPKNMRENQ----------

CBA-1     296 PKLTTAASGFTAAITPLFMVPLMFFA-
CBA-2.1   258 -----GSGFTPAIAFTSLLPFLLMMS
CBA-2.2   254 -----ESGFTPAIAFTSLLPFLLMMS
```

Figure 2

| | | |
|---|---|---|
| CBA-1_cDNA | 1 | ATGATGCTGCTCTTCGCCTTGTCTACTCTTGTCACCTTCGCCTTCTGCGATGGTGAAAACACTATACTTTATCCAATGTAGAATTCCATACTCCAGTAT |
| CBA-1_gene | 1 | ATGATGCTGCTCTTCGCCTTGTCTACTCTTGTCACCTTCGCCTTCTGCGATGGTGAAAACACTATACTTTATCCAATGTAGAATTCCATACTCCAGTAT |
| CBA-1_cDNA | 101 | CCAGTGTAAAGCTGCTTAAAGAATACAGTAGCAATCAGGAATCAATGGCCGTTATTATGATGCTAACCG------------------------- |
| CBA-1_gene | 101 | CCAGTGTAAAGCTGCTTAAAGAATACAGTAGCAATCAGGAATCAATGGCCGTTATTATGATGCTAACCGGTAGGAAATTATATGCATAATTCATAATTCG |
| CBA-1_cDNA | 170 | ---AAATGCCAAACACATCAGGAAAGCTTACCGATGGCAAAGTTCATGTGGCCAATGATAACGTTAAATGTGCTGATTTGGCTCTGATTTGCTTATCAAGAACT |
| CBA-1_gene | 201 | CAGAAATGCCAAACACATCAGGAAAGCTTACCGATGGCAAAGTTCATGTGGCCAATGATAACGTTAAATGTGCTGATTTGGCTCTGATTTGCTTATCAAGAACT |
| CBA-1_cDNA | 267 | CAAAAAGGCCGGCAAGGTGACATCATGGAGTCCAACTGATGAGTCCAACTGATGACAACGATAAGGTGTACCTCATGGAATCTGGTTCATGAGGGCGTCTATGAGACTGAT |
| CBA-1_gene | 301 | CAAAAAGGCCGGCAAGGTGACATCATGGAGTCCAACTGATGAGTCCAACTGATGACAACGATAAGGTGTACCTCATGGAATCTGGTTCATGAGGGCGTCTATGAGACTGAT |
| CBA-1_cDNA | 367 | AAGATGT--------------------------------------- |
| CBA-1_gene | 401 | AAGATGTGTAAGTAGAGATGTGTTTATCAACCGTATTGGGGTATACTATACAATTATTCAGTTGCTATATGAAGTTTCTGGTTTAATAATTGTGCCATGTCC |
| CBA-1_cDNA | 374 | ----------------------------TCGAGGTTTACAAGACCCTGACCGATCCTGAGGACCCAAGCGAAGTTACT |
| CBA-1_gene | 501 | ACGCCATTTGCACTATTAGCACTGTGTTTTCTGGTGCATTAATTAATCGTTCCTGAGTTGTTTCAGTCGAGGTTTACAAGACCCTGACCGATCCTGAGGACCCAAGCGAAGTTACT |
| CBA-1_cDNA | 424 | CGCTTGACAACTGTTTCTGGTGCTCTCAAAGCCAGCCTGCTGGTACTACTGATGGTGTCTCGGGTAGCGCTGCTAGTCCTCTACTTCTTAGTTCTTACTGACCA |
| CBA-1_gene | 601 | CGCTTGACAACTGTTTCTGGTGCTCTCAAAGCCAGCCTGCTGGTACTACTGATGGTGTCTCGGGTAGCGCTGCTAGTCCTCTACTTCTTAGTTCTTACTGACCA |
| CBA-1_cDNA | 524 | CTGGTTCCACTACTTCCCATTCCCAATACACCCAAACATCCTACAGTGCAGGATCTAGCGTTCATAAAAGCGCTGTGTTGCTCCACTCAGAGTACCACTCCTGATAATGCT |
| CBA-1_gene | 701 | CTGGTTCCACTACTTCCCATTCCCAATACACCCAAACATCCTACAGTGCAGGATCTAGCGTTCATAAAAGCGCTGTGTTGCTCCACTCAGAGTACCACTCCTGATAATGCT |
| CBA-1_cDNA | 624 | GGCATCCATGCTTACCACCCAAACATCCTACAGTGCAGGATCTAGCGTTCATAAAAGCGCTGTGTTGCTCCACTCAGAGTACCACTCCTGATAATGCT |
| CBA-1_gene | 801 | GGCATCCATGCTTACCACCCAAACATCCTACAGTGCAGGATCTAGCGTTCATAAAAGCGCTGTGTTGCTCCACTCAGAGTACCACTCCTGATAATGCT |
| CBA-1_cDNA | 724 | GAATCTGGGCGCAAAGCAAAGCAAAGCTGCGGTTCAGGAACCTAAGAACCTAAGAACCTAAGCAAATGTTTGATGATTCTGACCAAGTGTGATCTTAAGGCCGAAGTTACCGAGGAAC |
| CBA-1_gene | 901 | GAATCTGGGCGCAAAGCAAAGCAAAGCTGCGGTTCAGGAACCTAAGAACCTAAGCAAATGTTTGATGATTCTGACCAAGTGTGATCTTAAGGCCGAAGTTACCGAGGAAC |
| CBA-1_cDNA | 824 | AGATAAGAAGCCAAGGAAACCAGAAAGCAATGGGTCTTCTTCTGAACCACTGCTGCTTCTCCTAAACTTACTACCGCTGCTTCTGATTCACTGCCGC |
| CBA-1_gene | 1001 | AGATAAGAAGCCAAGGAAACCAGAAAGCAATGGGTCTTCTTCTGAACCACTGCTGCTTCTCCTAAACTTACTACCGCTGCTTCTGATTCACTGCCGC |
| CBA-1_cDNA | 924 | CATTACCCCCTTGTTCATGGTCCCACTCATGTTTTTCGCCTAA |
| CBA-1_gene | 1101 | CATTACCCCCTTGTTCATGGTCCCACTCATGTTTTTCGCCTAA |

CANINE BABESIOSIS VACCINE ANTIGEN

CROSS-REFERENCE TO RELATED APPLICATIONS

This application is a divisional application of U.S. patent application Ser. No. 13/997,805, filed on Jun. 25, 2013, now abandoned; which is a national stage entry under 35 U.S.C. §371 of PCT/EP2011/074120, filed on Dec. 28, 2011, which claims priority to U.S. Provisional Application No. 61/430,298, filed on Jan. 6, 2011, and EP Application No. EP10197303.0, filed on Dec. 29, 2010. The content of PCT/EP2011/074120 is hereby incorporated by reference in its entirety.

The present invention relates to the field of veterinary parasitology, especially of canine Babesiosis. In particular the invention relates to a polypeptide being a novel canine *Babesia* antigen (CBA), or fragments thereof, and to compositions comprising this antigen, to nucleic acids encoding the antigen, antibodies against the antigen, and medical uses of this antigen, fragments, antibodies, or encoding nucleic acids. In particular the invention relates to the use of such components in vaccines against canine Babesiosis.

The protozoal micro-organisms of the genus *Babesia* are tick-borne intra-erythrocytic parasites of the order Piroplasmida, in the phylum Apicomplexa. *Babesia* species are subdivided along several criteria, amongst others by the tick vector(s) present in the environment that can transmit a specific species of *Babesia* parasite. The tick vector in turn determines the geographical spread of the parasite and the vertebrate host that is infected.

Infection of a vertebrate host with *Babesia* parasites causes a disease, Babesiosis, also called: *Piroplasmosis*, with a wide variation in symptoms and severity; the disease and its symptoms were first described in 1904 (Nuttall, J. Hyg. (Lond.) vol. 4, p. 219-257).

In prevention of Babesiosis several approaches have been employed such as for example by tick control. This is achieved mainly by treating the host on which the ticks feed with drugs. Such treatments comprise dips, poor-ons, or parenteral drugs which repel or kill the ticks. Disadvantages of such methods are the cost price of such treatments which may need to be repeated frequently; possible drug-toxicity; possible drug residues existing in the meat or milk of food animals; and the build-up of drug-resistance among the tick population. The same disadvantages apply in the drug-based treatment of animals that have already become infected with *Babesia*.

Therefore, an alternative is the prevention or amelioration of Babesiosis by vaccination of a target animal, which in this case is the host on which the ticks may feed, and which host as a result may become infected with *Babesia*. Commonly, such vaccines comprise an immunologically effective amount of an antigenic molecule of the tick, or of the *Babesia* parasite, in a pharmaceutically acceptable carrier. However, because a parasite such as *Babesia* is a highly complex organism, it has proven extremely difficult to identify individual antigens for vaccination of a target animal, that allow the generation of an immune response that is quick, safe and effective. In fact, this is one of the greatest challenges for parasite immunology in general today.

*Babesia* parasites can infect a wide variety of vertebrate animals, but the infections of domestic mammals and of humans are of most relevance to veterinary practice and medicine. Although several *Babesia* species can infect canine animals, the most prevalent canine *Babesia* are for Europe: *B. canis*, and for Sub-Saharan and Southern Africa: *B. rossi*.

The canine Babesias were in the past taxonomically classified as subspecies of *B. canis*, thus as: *B. canis canis*, and *B. canis rossi*, etc., following a proposal for a trinomial nomenclature system (Uilenberg et al., 1989, Vet. Quart., vol. 1, p. 33-40). However, in recent years, more and more species of *Babesia* were described in dogs, and information was obtained on their life-cycle, their arthropod vectors, and the characterisation of their genetic material. This led to the notion, that these subspecies under *Babesia canis* should be classified each as a proper species by themselves. This is reviewed in Schetters, 2005 (Trends in Parasitology, vol. 21, p. 179-184). This new classification is used throughout this text.

*B. canis* and *B. rossi* are so-called "large" species of canine *Babesia*, i.e. larger than the radius of an erythrocyte. *B. canis* is transmitted by tick vectors of the genus *Dermacentor*, and *B. rossi* by Haemaphysalis ticks. *B. rossi* parasites are the most pathogenic of the canine *Babesia* species; *B. canis* parasites are somewhat less pathogenic. The main symptoms of disease are anaemia or an immuno-pathology resembling malaria. Other symptoms are renal failure, pulmonary oedema, and general shock response. Animals that do recover may suffer relapses later on. A review is e.g. Jacobson & Clark (1994, J. of S. Afr. Vet. Assoc., vol. 65, p. 134-145). Vaccines commonly aim at preventing or reducing the (level of) infection with a micro-organism, or the disease caused by that infection. Vaccines for canine Babesiosis have been described before. For instance by Ristic et al. (1988, in: Babesiosis of domestic animals and man, ed. M. Ristic, p. 163-189, CRC Press Inc., Boca Raton, Fla., ISBN: 0849349087), and: Schetters et al. (1992, Par. Immunol. vol. 14, p. 295-305).

These vaccines employed soluble parasite antigens (SPA), which are parasite exoantigens that are either released by the parasite, or result from ruptured or dying parasites. When produced in vivo, for example such as described by Sibinovic et al. (1967, The J. of Parasitology, vol. 53, p. 919-923) these antigens accumulate in the plasma of infected canine hosts; alternatively, when produced in vitro they accumulate into the supernatant of the erythrocyte culture in which the *Babesia* are amplified (Schetters et al., 1992, Parasite Immunology, vol. 14, p. 295-305). SPA from a *B. canis* culture was used to protect dogs against infection with that same (i.e. homologous=from a source, isolate, or strain that is the same as the one that was used in the cultures to produce the SPA antigen comprised in the vaccine) *B. canis* strain. Remarkably, a homologous vaccination was not effective for *B. rossi*: SPA from a culture of *B. rossi* parasites could not protect dogs against *B. rossi* induced infection and disease. This required a mixture of SPA from cultures of both *B. canis* and *B. rossi* SPA, as described in EP 691.131; dogs could then be effectively immunized with *B. rossi* and *B. canis* culture-derived SPA, supplemented with Saponin as adjuvant, and developed a protective immune response against both *B. canis* and *B. rossi* parasites, and parasite-infected erythrocytes.

The production of SPA in an in vitro culture at an industrial scale has been optimised by MSD Animal Health, in a proprietary process for the production of its vaccine: Nobivac® Piro (Schetters et al., 1995, Parasitol. Today, vol. 11, p. 456-462). Nevertheless, the in vitro or in vivo propagation of live parasites in an industrial setting has inherent disadvantages, such as that it requires extensive controls to ensure the quality and the reproducibility of the product, at considerable costs. It may also be desirable to reduce the use of starting materials from biological origin such as, normal canine blood and serum.

A further disadvantage of the known crude SPA based *Babesia* vaccines is that they contain remains of lysed normal erythrocytes, which themselves could cause auto-immune responses against the red blood cells of the vaccinated animal. For those reasons, there is an urgent need for a canine Babesiosis vaccine that circumvents at least some of the above disadvantages.

It is an object of the present invention to provide an antigenic component that can be used to produce an effective, safe and reliable vaccine for protection against the infection and/or the disease caused by canine *Babesia* parasites; the vaccine component should overcome the disadvantages of classical SPA vaccines, and protect not only against homologous, but also against heterologous *Babesia* parasite infection.

Surprisingly it was found that the disadvantages of the prior art could be overcome, and the objectives be met, by a specific isolated polypeptide which could be used to produce a vaccine for canines that is effective against *Babesia* parasite infection and the disease that causes. The use of the specific polypeptide overcomes the need to use a crude mixture of soluble parasite (exo-) antigens as in the known vaccines against canine Babesiosis.

The purified and isolated polypeptide was tentatively termed "canine *Babesia* antigen" (CBA), and was found to belong to a class of CBA protein antigens with representatives in different canine *Babesia* parasite species.

The different CBA polypeptides have in common a calculated molecular weight of about 30 kDa (e.g. between about 29 and 33 kDa), a relatively acid pI (e.g. between about 4.6-4.8), and have an N-terminal signal sequence (e.g. between about 16-18 amino acids) which corresponds to the fact that the CAB polypeptides are actively secreted by the *Babesia* upon infection of an erythrocyte.

*Babesia canis* was found to express one CBA antigen, named herein as CBA-1, whereas *B. rossi* expressed two CBA homologs, referred to herein as CBA-2.1 and -2.2.

Similarly, the second conserved sequence area: VLMVLTKCNLKMHVTEEQL (SEQ ID NO: 3) represented by the C-terminus of CBA-2.1, was also compared to known polypeptides. The best match was found to have only 11 of the 19 amino acids, which represents an amino acid identity of 57.9%. In contrast, the amino acid sequence identity between the corresponding regions of the *B. canis* and *B. rossi* CBA polypeptides themselves is significantly higher, at over 68%, as is presented in Table 2.

TABLE 1

List of sequence identifiers used herein

| SEQ ID NO: | Description: |
|---|---|
| 1 | Characterising region 1 near N-terminus of *B. rossi* CBA-2.1 and CBA-2.2 |
| 2 | Char. region 1 near N-term. of *B. canis* CBA-1 |
| 3 | Char. region 2 near C-term. of *B. rossi* CBA-2.1 |
| 4 | Char. region 2 near C-term. of *B. rossi* CBA-2.2 |
| 5 | Char. region 2 near C-term. of *B. canis* CBA-1 |
| 6 | Amino acid sequence of *B. canis* CBA-1 |
| 7 | Amino acid sequence of *B. rossi* CBA-2.1 |
| 8 | Amino acid sequence of *B. rossi* CBA-2.2 |
| 9 | mRNA sequence of *B. canis* CBA-1 (as cDNA) |
| 10 | mRNA sequence of *B. rossi* CBA-2.1 (as cDNA) |
| 11 | mRNA sequence of *B. rossi* CBA-2.2 (as cDNA) |
| 12 | Genomic sequence of *B. canis* CBA-1 |
| 13 | Genomic sequence of *B. rossi* CBA-2.1 |
| 14 | Genomic sequence of *B. rossi* CBA-2.2 |
| 15 | Core aa sequence of characterising region 1 |

TABLE 2

Amino acid sequence identity between the amino acid sequences of the characterising regions of the CBA proteins from different canine Babesia species.

| amino acid sequence | Characterising region 1: MLLSNVSFPQPVSSVKLLEEY | Characterising region 2: VLMVLTKCNLKMHVTEEQL |
|---|---|---|
| B. canis CBA-1 | 16/21 (76.2%) | 14/19 (73.7%) |
| B. rossi CBA-2.1 | 21/21 (100%) | 19/19 (100%) |
| B. rossi CBA-2.2 | 21/21 (100%) | 13/19 (68.4%) |

The members of this novel class of *Babesia* antigens share conserved amino acid sequence regions, each of which characterises the CBA polypeptides and distinguishes them from known polypeptides.

These conserved sequence regions are presented herein as SEQ ID NO's 1-5 (see Table 1), and were surprisingly found to be located at the N- and C-terminal ends of the CBA polypeptide, with the N-terminal characterising region being located immediately downstream of the signal sequence. The central region of the CBA polypeptides is less conserved.

The first of the two characterising regions of the CBA polypeptides is represented by the N-terminus of the CBA polypeptide from *B. rossi*; in fact the sequence is the same for both CBA-2.1 and CBA-2.2: MLLSNVSFPQPVSSVKLLEEY (SEQ ID NO: 1).

When compared to known polypeptides, the best matches to the amino acids of SEQ ID NO: 1 were found to have an amino acid identity of only 11 of the 21 amino acids, which is an identity of 52.3%.

Similarly, characterising region 2 (SEQ ID NO: 3) appeared in canine *Babesia* species with an identity of at least 68%, whereas the best homologue in the public databases was not more than 57% identical. In addition, a Blast search for a molecule containing both regions did not produce any matches.

The polypeptides identified herein are therefore characterized by the presence of a region of high homology or identity with an amino acid sequence according to either or both of SEQ ID NO's 1 and 2.

The invention therefore relates to an isolated polypeptide comprising an amino acid sequence having an amino acid sequence identity greater than 53% with the amino acid sequence according to SEQ ID NO: 1, and/or having an amino acid sequence identity greater than 58% with the amino acid sequence according to SEQ ID NO: 3, wherein said polypeptide is capable of inducing an immune response against a canine *Babesia* parasite and/or its products or effects.

For the invention, a "polypeptide" refers to a molecular chain of amino acids. A polypeptide is not of a specific length, structure or shape and can, if required, be modified in vivo or in vitro, by, e.g. glycosylation, amidation, carboxylation, phosphorylation, pegylation, or changes in spatial folding. Inter alia, proteins, peptides, oligopeptides are included within the definition of polypeptide. A polypeptide can be of biologic and/or of synthetic origin.

The term "isolated" is to be interpreted as: isolated from its natural environment. This also applies to the purification of the CBA polypeptide (or its encoding nucleic acid) in compositions to amounts that are higher than the amount of other substances in that composition, preferably in a much higher amount such that the polypeptide or nucleic acid makes up for 70% or 80% or 90% or more of the total composition. Preferably, the polypeptide or nucleic acid makes up for 92%, 94%, 96%, 97%, 98%, or even 99% of the total composition.

The term "amino acid sequence identity" is to be interpreted as the percentage of identical amino acids at corresponding positions when two amino acid sequences are optimally aligned over their full length. Alignment can conveniently be performed with a computer program, for instance with Blast® or ClustalW®, using default parameters.

The term "capable of inducing an immune response" refers to the capacity of the CBA polypeptides according to the invention to induce an immune response that is effective against infection or disease caused by canine *Babesia* parasites. Such an effective immune response is for example the prophylaxis, prevention or amelioration of Babesiosis and/or of the parasitaemia of *Babesia* parasites in canines.

Such an immune response can take different forms, and can function via different branches of the immune system, from the innate and/or the acquired immune system, and may be of the cellular and/or of the humoral type. The presence or the induction of such an immune response can be detected by well known techniques, and additionally in ways as described herein. For example, antibodies against CBA can be detected e.g. by Elisa, immunofluorescence, immunoblot etc. The cellular immune response can be detected by lymphocyte stimulation assays or in vivo skin reactions. Further methods include the monitoring of the immunised patients' symptoms or its physiological responses typically associated with *Babesia* infection and disease such as: packed cell volume (also: haematocrit), number of infected erythrocytes, spleen size, etc., in addition to general behavioural scores.

Ultimately, the polypeptides of the invention (when applied in a vaccine) are capable of preventing or reducing the infection and/or the disease caused by that infection resulting from canine *Babesia* parasite infection.

A "canine *Babesia*" is a *Babesia* parasite that can infect a canine animal. Typically these are *Babesia canis, B. rossi, B. vogeli* and *B. gibsoni*, but other species of *Babesia* have also been described or associated with canine infections (Uilenberg, 2006, Veterinary Parasitology vol. 138, p. 3-10). With respect to the precise taxonomic classification of *Babesia*, the skilled person will realise this may change over time as new insights lead to reclassification into new or other taxonomic groups. However, as this does not change the characteristics and/or the protein repertoire of the organism involved, only its classification, such re-classified organisms are considered to be within the scope of the invention. "Canines" relates to all (sub-)species of Canidae, mainly dogs, wolves and foxes, as well as any mixed breeds.

In addition, the immunologic efficacy of the polypeptides according to the invention against Babesiosis, affects different *Babesia* species in a different way; vaccination may prevent parasitaemia as well as disease for one species, but only counter disease for another (see e.g. Schetters et al., 1997, Parasitology, vol. 115, p. 485-493).

The inventors found that it was in no way straightforward to isolate and characterise the CBA polypeptides according to the invention from crude antigen preparations. This was mainly because routine techniques either did not work, or did not present the required data. As a result several adaptations and non-obvious combinations of known techniques have had to be applied to arrive at the desired polypeptides. For example:

Only the mixture of SPA exoantigens was known as effective vaccine: both commercial *Babesia* vaccines available at the filing date of the present invention, employ a crude mixture of *Babesia* exoantigens as vaccine component. Also, in the many decades of research into canine Babesiosis, no single compounds have yet made it to a successful commercial vaccine. Therefore is was commonly accepted that the protection against Babesiosis provided by immunizing dogs with SPA was due to a heterogeneous immune reaction involving a multitude of antigens, and which could not be attributed to a single protein. This would dissuade any person skilled in the art to even embark on investigating single vaccine antigens.

Further, a lack of highly productive culturing techniques for *B. canis* and *B. rossi* would prevent a skilled person to obtain sufficient amounts of any single *Babesia* antigen for characterisation. Thus, although routine culturing techniques have been described, it required the highly productive in vitro culturing technique that is proprietary to the applicant, to be able to generate sufficient amounts of *Babesia* proteins for the identification of CBA as individual components.

Also, the CBA polypeptide of the invention could not be isolated directly from SPA, because the SPA is a crude mixture of many different components from erythrocytes, from *Babesia*, and from components of the animal serum that is required for the culture, up to levels of 40% v/v.

When an attempt was made to isolate CBA from coomassie brilliant blue-stained gels of complete SPA, this resulted in numerous failures, mainly because all fractions were heavily contaminated with serum proteins and haemoglobin from the erythrocytes in the culture, but also the plethora of bands, from low to high molecular weight, completely blocked the availability of any single individual protein band. Experiments aimed at purification using single-step procedures such as protein-A affinity chromatography, ion exchange chromatography and size exclusion columns was without any success. Finally isolation of CBA from SPA was achieved by using a complex purification protocol which involved adapted culture techniques, and a specific combination of a number of consecutive separation- and precipitation techniques out of the ordinary.

Ultimately this yielded sufficient quantities of the CBA polypeptide for further analysis.

However, it was not possible to visualize any isolated CBA polypeptide by standard immunoblotting techniques: the inventors were surprised to find that CBA is not recognised on an immunoblot of total parasite lysate or from SPA; not by regular antiserum from canines immunised with SPA, nor by antiserum from a canine that was infected with *Babesia*. This is because either the amount of CBA in SPA is too low, or the form of CBA in SPA is not suited for immuno-blot recognition. Remarkably, CBA could only be identified on an immunoblot when the inventors used serum from a canine that had first been vaccinated multiple times with SPA, and subsequently had been challenge-infected with *Babesia*, so-called: vaccination-challenge serum.

A further restriction was that this vaccination-challenge serum needed to be obtained at a very specific period after challenge: between day 6 and day 11. Serum from before or after that period was not able to show the faint reactivity with a CBA polypeptide, having a relative molecular weight of approximately 41 kDa.

In further analysis, the fact that only the N- and C-termini of the various CBA polypeptides were conserved, and consequently that the bulk of the (mature) polypeptides had little sequence conservation, made it very hard to identify the corresponding gene and mRNA sequences coding for these polypeptides in the Babesia genome. In addition, no genomic sequences were known for either B. canis or B. rossi, so that these genomes had to be sequenced, analysed for possible open reading frames, and the regions of interest had to be obtained by PCR. This last step required extensive use of degenerated primers because of the sequence differences found in the CBA genes.

In an embodiment the amino acid sequence identity to either of SEQ ID NO's 1 and/or 2 is at least 58%, preferably at least 59% such as 60% or 62%, 64%, 66%, 68%, 70%, 71%, 73%, 75% or 76%.

In an embodiment, the polypeptides according to the invention are characterized in that they comprise an amino acid sequence that has an amino acid sequence identity greater than 58% with one or more amino acid sequence(s) selected from the group consisting of: SEQ ID NO: 1, SEQ ID NO: 2, SEQ ID NO: 3, SEQ ID NO: 4 and SEQ ID NO: 5.

For the invention, the transitional phrases "comprising" and "consisting of" define the scope of a claim with respect to what unrecited additional components or steps, if any, are excluded from the scope of the claim.

The transitional term "comprising", which is synonymous with "including," "containing," or "characterized by," is inclusive or open-ended and does not exclude additional, unrecited elements or method steps.

The phrase "group consisting of" is a closed term, used in claim drafting to signal a "Markush group" that is by its nature closed and is used to distinguish or identify the various members of the group.

The transitional phrase "consisting of" excludes any element, step, or ingredient not specified in the claim.

The inventors finally succeeded in obtaining the complete amino acid sequences of a number of CBA polypeptides. These are presented herein as SEQ ID NO's: 6, 7 and 8.

When compared to each other, these full length polypeptide sequences demonstrated the remarkable conservation of their N- and C-termini, with less conservation in their main central part, see FIG. 1. In short, the amino acid sequence identity between these full sequences is as represented in Table 3.

When compared to known polypeptides, no significant full length matches could be identified.

TABLE 3

Amino acid sequence identity between the full length amino acid sequences of CBA polypeptides described herein.

| % aa seq. identity | B. canis CBA-1 (SEQ ID NO: 6) | B. rossi CBA-2.1 (SEQ ID NO: 7) |
|---|---|---|
| B. rossi CBA-2.1 (SEQ ID NO: 7) | 29 | x |
| B. rossi CBA-2.2 (SEQ ID NO: 8) | 35 | 43 |

Therefore in an embodiment the CBA polypeptides according to the invention are characterised in that they have an amino acid sequence identity greater than 29% with at least one amino acid sequence selected from the group consisting of SEQ ID NO: 6, SEQ ID NO: 7 and SEQ ID NO: 8.

The identity percentage for this embodiment is to be calculated over the full length of the CBA polypeptide as in SEQ ID NO: 6, 7, or 8. The term "greater than 29%" may be interpreted as at least 30%, 32%, 35%, 39%, 43%, 50%, 55%, 60%, 65%, 70%, 75%, 80%, 85%, 88%, 90%, 92%, 94%, 96%, 98%, or even more than 98%.

It was found that the characterising region no. 1 itself comprises a core sequence that is perfectly conserved between CBA polypeptides from B. canis and B. rossi. This sequence: PVSSVKLL (SEQ ID NO: 15) was not found in any known polypeptide with an 8/8 (100%) amino acid sequence identity; therefore it may serve to further characterise a CBA polypeptide according to the invention.

Therefore, in a further preferred embodiment, the polypeptide according to the invention comprises an amino acid sequence that is: PVSSVKLL (SEQ ID NO: 15).

Preferably, the SEQ ID NO: 15 sequence is present in a polypeptide according to the invention in the N-terminal region of the mature polypeptide.

In an embodiment, the invention also relates to an immunogenic fragment of the polypeptide according to the invention.

Such an immunogenic fragment can be obtained in a well known way, using the information provided herein. For example by generating tryptic digests of the CBA polypeptides, and testing the immunogenicity of the fragments obtained. Or the fragments can be synthesized and tested as in the well known PEPSCAN method (WO 84/003564, WO 86/006487, and Geysen et al., Proc. Natl. Acad. Sci. USA, 1984, vol. 81, p. 3998-4002). Alternatively, immunogenically relevant areas can be predicted by using well known computer programs. An illustration of the effectiveness of using these methods was published by Margalit et al. (1987, J. of Immunol., vol. 138, p. 2213-2229) who describe success rates of 75% in the prediction of T-cell epitopes.

As is well known, polypeptides in order to be immunogenic need to be of a minimal length; typically 8-11 aa for MHC I receptor binding, and 11-15 aa for MHC II receptor binding (reviewed e.g. by Germain & Margulies, 1993, Annu. Rev. Immunol., vol. 11, p. 403-450). Therefore, for the invention, an immunogenic fragment of the polypeptide according to the invention is at least 8 amino acids in length.

Polypeptide fragments that still do not generate an effective immune response may be presented to a target's immune system attached to, or in the context of a carrier molecule. Well known carriers are bacterial toxoids, such as Tetanus toxoid or Diphtheria toxoid; alternatively KLH, BSA, or bacterial cell-wall components (derived from) lipid A, etc. may be used. Also polymers may be useful, or other particles or repeated structures such as virus like particles etc. The coupling to a carrier molecule can be done by methods known in the art, using chemical or physical techniques.

The CBA polypeptides according to the invention, or the immunogenic fragment thereof, may be of biological or synthetic origin, and may be obtained by isolation, purification, assembly etc. The polypeptides can be isolated from in vivo or in vitro cultures of canine Babesia parasites. However the polypeptides are more conveniently produced by using a recombinant expression technology, by expression of a nucleotide sequence encoding the polypeptides or the fragment.

Therefore, in a further aspect the invention relates to an isolated nucleotide sequence that is capable of encoding the polypeptide, or the immunogenic fragment thereof, according to the invention.

The concept of a nucleotide sequence being "capable of encoding" a polypeptide is well known in the art, and relates to the central dogma of molecular biology on gene-expression and protein production: a DNA is transcribed into RNA, and the RNA is translated into a protein. Typically such a nucleotide sequence capable of encoding a polypeptide is called an: open reading frame (ORF), indicating that no undesired stop-codons are present that would prematurely terminate the translation into protein by a ribosome. Said nucleotide sequence may be a gene (i.e. an ORF encoding a complete protein), or be a gene-fragment. It may be of natural or synthetic origin.

The invention advantageously provides the mRNA and the genomic sequences for a number of CBA polypeptides. As indicated, the genome of B. rossi was found to comprise two separate genes encoding two different versions of the CBA polypeptide, the genome of B. canis only contained one CBA gene. The CBA mRNA sequences (in cDNA format) are presented in SEQ ID NO's: 9-11, and the CBA genomic sequences in SEQ ID NO's: 12-14 (see Table 1).

When the mRNA sequences were identified and analysed, all corresponding CBA genes were found to contain untranslated regions of between 15-19% of the complete gene. Although the lengths of the different CBA genes differ, the location and division of these introns was highly similar, with all CBA genes possessing two introns located approximately between the nucleotide numbers 170 and 200 and between 400 and 550 (see Table 4, and FIG. 2). This conserved gene-organisation is a further demonstration of the relatedness of the members of the class of CBA polypeptides identified herein.

TABLE 4

Location of introns in CBA genes

| CBA gene | Intron location (nucleotides numbers) | | % of gene is intron |
|---|---|---|---|
| B. canis CBA-1 (SEQ ID NO: 12) | 170-203 | 408-550 | 15 |
| B. rossi CBA-2.1 (SEQ ID NO: 13) | 173-207 | 406-569 | 19 |
| B. rossi CBA-2.2 (SEQ ID NO: 14) | 170-204 | 406-552 | 18 |

The CBA genes, or preferably the corresponding cDNA sequences, can conveniently be employed for a variety of goals, e.g. to express and produce the CBA polypeptides according to the invention. However, as is well known in the art, different nucleic acids can encode one and the same protein. This is a result of what is known in molecular biology as "wobble", or the "degeneracy of the genetic code", wherein several codons or triplets of mRNA will cause the same amino acid to be attached to the chain of amino acids growing in the ribosome during translation. It is most prevalent in the second and especially the third base of each triplet encoding an amino acid. This phenomenon can result in a heterology of about 30% for two different nucleic acids that still encode the same protein. Therefore, two nucleic acids having a nucleotide sequence identity of only about 70% can still encode one and the same protein.

Therefore, in an embodiment the nucleotide sequence according to the invention has a nucleotide sequence identity greater than 70% with at least one nucleotide sequence selected from the group consisting of SEQ ID NO: 9, SEQ ID NO: 10, SEQ ID NO: 11, SEQ ID NO: 12, SEQ ID NO: 13 and SEQ ID NO: 14.

As is also well known, an alternative way to characterise a nucleotide sequence by its nucleotide sequence identity level, is not by computer analysis, but by a physical measurement; conveniently this can be done by an assay testing hybridisation under conditions of increasing stringency.

Therefore, in an alternate embodiment, the nucleotide sequence according to the invention can hybridise under stringent conditions to at least one nucleotide sequence selected from the group consisting of SEQ ID NO: 9, SEQ ID NO: 10, SEQ ID NO: 11, SEQ ID NO: 12, SEQ ID NO: 13 and SEQ ID NO: 14.

The term "hybridise" refers to the process of binding (also called: annealing, or: sequence-specific basepairing) between two strands of nucleic acids. In a hybridization process the complementary regions of a target nucleic acid and a probe will find each other, anneal and become attached. The nucleic acids can be DNA or RNA, as long as they are single stranded and unfolded. Under the proper conditions, target and probe will bond by forming hydrogen-bridges between A and T, and between G and C nucleotides.

Typically the target nucleic acid will be a larger molecule of DNA (a plasmid, a chromosome, or genome), or a (m)RNA, and the probe is usually a DNA (because that is more stable than RNA), single stranded, and smaller than the target, e.g. between 50 and 5000 bases.

"Stringency" in practice is determined mainly as a function of salt concentration and temperature used for the hybridisation and the washing steps in a hybridisation test protocol. The qualification of stringent conditions follows from the formula for the melting temperature Tm from Meinkoth & Wahl (1984, Anal. Biochem., vol. 138, p. 267-284):

$$Tm=[81.5° C.+16.6(\log M)+0.41(\% GC)-0.61(\% \text{formamide})-500/L]-1° C./1\% \text{ mismatch}$$

In this formula, M is the molarity of monovalent cations; % GC is the percentage of guanosine and cytosine nucleotides in the DNA; L is the length of the hybrid in base pairs; and 'mismatch' is the lack of an identical match.

As is well known, high salt and low temperature are "low" stringent conditions; and low salt and high temperature are highly stringent. By selecting specific hybridization and washing conditions, one may set a certain level of stringency, and thereby determine the minimal level of thermal stability that needs to exist between the DNA-DNA (or RNA-DNA) duplexes that will form, and will sustain.

The standard buffer used to set the stringency is SSC buffer (Saline sodium citrate), wherein the standard "20×" SSC buffer contains 3 Molar NaCl and 0.3 M citrate in water at pH 7. This way, a very low stringency would be washing in 20×SSC at room temperature (3 M salt, and 20° C.), and the highest stringency would be boiling in distilled water (no salt, and 100° C.).

This is also extensively described in handbooks such as Current Protocols in Molecular Biology, John Wiley & Sons, N.Y. (1989), 6.3.1-6.3.6; Basic Methods in Molecular Biology, Elsevier Science Publishing Co., Inc., N.Y. (1986), pp. 75 78, and 84-87; Molecular Cloning, ed. Sambrook et al., Cold Spring Harbor Laboratory, N.Y. (1982), pp. 387-389, and 2001.

For the invention "stringent conditions" are those conditions under which a nucleotide sequence can still hybridise if it has a mismatch of 30% or less (i.e. if there is nucleotide sequence identity of more than 70%) to a nucleotide sequence according to the invention. More preferably, conditions under which a nucleotide sequence having about 70%, at least 75%, at least 80%, at least 85%, at least 90%, or at least 95% nucleotide sequence identity, can remain hybridized to a nucleotide sequence according to the invention.

A preferred, non-limiting example of stringent hybridization conditions for the invention is hybridization in 2-6×SSC and 0.5% SDS at about 45° C., followed by one or more washes (e.g., about 5 to 30 min each) in 0.5-2×SSC, 0.1% SDS at 45-65° C.

The nucleotide sequence according to the invention can conveniently be used in a variety of ways. One example is for diagnostic purposes, via a variety of methods and technologies, for example for the detection of an infection of a canine host with *Babesia* parasites.

Routinely nucleotide sequences such as those according to the invention are conveniently manipulated in the context of a vector, such as a DNA plasmid, enabling their amplification in e.g. bacterial cultures, and their manipulation in a variety of molecular biological techniques. A wide variety of suitable plasmid vectors is available commercially.

When the nucleotide sequences according to the invention are to be used for the expression of polypeptides, they need to be in a context that allows the transcription into mRNA and translation into protein. In particular the nucleotide sequence needs to be provided with the proper regulatory signals to initiate transcription and translation, for instance being operatively linked to a promoter and a stop codon when the nucleic acid is a DNA; or to a polyA tail when the nucleic acid is an mRNA.

Therefore, in a further aspect, the invention relates to an isolated nucleic acid comprising the nucleotide sequence according to the invention.

In a preferred embodiment the nucleotide sequence is under the control of a functionally linked promoter.

The elements of the term "nucleotide sequence [ . . . ] under the control of a functionally linked promoter" are all well known in the art; a 'promoter' is a regulatory section of DNA that can initiate RNA transcription. For the promoter to achieve this effect, it needs to 'control' a section of DNA that can be transcribed, such as an ORF or a gene. The element of being 'functionally linked' to the reading frame that is to be expressed, means that no sequence elements are present in between these two that would prevent the promoters' function. Typically a promoter is located immediately upstream of the ATG startcodon of an ORF. It is obvious to those skilled in the art that the choice of a promoter for the invention extends to any eukaryotic, prokaryotic or viral promoter capable of directing the transcription, provided that the promoter is functional in the expression system used.

By way of a nucleic acid according to the invention, modifications can be made to the inserted nucleotide sequence e.g. insertions, deletions, or mutations, using common techniques of restriction enzyme digestion or by polymerase chain reaction (PCR).

For example, for the purpose of improvement of expression level, for the protein-purification or -detection after expression, or to make the polypeptide more immunogenic, additional nucleotide sequences may be added. This may result in the final nucleotide sequence comprised in the nucleic acid being larger than the sequences required for encoding a CBA polypeptide according to the invention. Also, when such additional elements are inserted in the reading frame, these become an integral part of the expressed CBA polypeptide; such fused polypeptides are also within the scope of the invention.

A preferred fused polypeptide for the invention is one as described in WO 2004/007525: by attaching a hydrophobic peptide to a core polypeptide, the fusion polypeptide more efficiently interacts with free saponin as an adjuvant. Examples of such hydrophobic peptides for fusion are described, for example a C-terminal section of decay accelerating factor (CD55).

A nucleic acid according to the invention can conveniently be used for so-called 'DNA vaccination'. In such an embodiment, a nucleic acid according to the invention is introduced into a target, where the nucleic acid is taken up into cells, the nucleotide sequence comprised becomes expressed, and the polypeptide produced is presented to the target's immune system generating an immune response. The DNA can be introduced in a variety of ways, and can be in different forms either as naked DNA or attached to or encapsulated by a carrier, for example gold-particles.

Direct vaccination with DNA encoding a polypeptide has been successful for many different proteins, as reviewed in e.g. Donnelly et al. (1993, The Immunologist, vol. 2, p. 20-26). For example in the field of anti-parasite vaccines, protection against e.g. *Plasmodium yoelli* has been obtained with DNA-vaccination with the *P. yoelli* circumsporozoite gene (Hoffman, S. et al., 1994, Vaccine, vol. 12, p. 1529-1533), and protection against *Leishmania major* has been obtained with DNA-vaccination with the *L. major* surface glycoprotein gp63 gene (Xu & Liew, 1994, Vaccine, vol. 12, p. 1534-1536).

A nucleic acid according to the invention can also be used advantageously to express and produce a CBA polypeptide, or an immunogenic fragment thereof, according to the invention. Recombinant expression systems for that purpose commonly employ a host cell, being cultured in vitro. Well known in the art are host cells from bacterial, yeast, fungal, insect, or vertebrate cell expression systems.

Therefore, in an embodiment, the invention relates to a host cell comprising a nucleotide sequence or a nucleic acid according to the invention.

A host cell to be used for expression of a CBA polypeptide according to the invention may be a cell of bacterial origin, e.g. from *Escherichia coli, Bacillus subtilis, Lactobacillus* sp. or *Caulobacter crescentus*, possibly in combination with the use of bacteria-derived plasmids or bacteriophages for expressing the sequence encoding a CBA polypeptide. The host cell may also be of eukaryotic origin, e.g. yeast-cells in combination with yeast-specific vector molecules; or higher eukaryotic cells, like insect cells (Luckow et al., 1988, Biotechnology, vol. 6, p. 47-55) in combination with vectors or recombinant baculoviruses; or plant cells in combination with e.g. Ti-plasmid based vectors or plant viral vectors (Barton, et al., 1983, Cell, vol. 32, p. 1033); or mammalian cells like Hela cells, Chinese Hamster Ovary cells, or Madin-Darby canine kidney-cells, also with appropriate vectors or recombinant viruses.

Next to these expression systems, plant cell, or parasite-based expression systems are attractive expression systems. Parasite expression systems are e.g. described in the French Patent Application, number 2,714,074. Plant cell expression systems for polypeptides for biological application are e.g. discussed by Fischer et al. (Eur. J. of Biochem. 1999, vol. 262, p. 810-816), and Larrick et al. (Biomol. Engin. 2001, vol. 18, p. 87-94).

Expression may also be performed in so-called cell-free expression systems. Such systems comprise all essential factors for expression of an appropriate recombinant nucleic acid, operably linked to a promoter that will function in that particular system. Examples are the *E. coli* lysate system (Roche, Basel, Switzerland), or the rabbit reticulocyte lysate system (Promega corp., Madison, USA).

An efficient way to express a nucleotide sequence or a nucleic acid according to the invention in a host cell, or even in an animal, is by their incorporation in a carrier that can enter host cells or a host animal. The carrier is a live recombinant carrier micro-organism (LRCM's) that can enter the host without damaging it.

Therefore, in an embodiment, the invention relates to a live recombinant carrier micro-organism comprising a nucleotide sequence or a nucleic acid according to the invention.

Such live recombinant carrier micro-organisms (LRCM's) are e.g. the bacteria, parasites, viruses and yeast cells, may all be used to infect a host animal. The replication of the LRCM in the host animal can be a way to produce the polypeptide or fragment according to the invention, which can subsequently be isolated and used for e.g. vaccination or diagnostic purposes. However, the LRCM can also conveniently be used for vaccination directly; for instance as a delivery vehicle for the polypeptide or the fragment according to the invention to that host animal, and in that way vaccinate the host animal. This route of presentation to the host's immune system may be more effective than by vaccination as a subunit protein with an adjuvant, because a replicating micro-organism is closer to the natural way of infection by Babesia, and can resemble the route CBA polypeptides or their immunogenic fragments are presented to the immune system in a natural infection. A further advantage of LRCM's is their self-propagation, so that only low amounts of the recombinant carrier are necessary for an immunisation.

For the invention convenient LRCM's are micro-organisms that can replicate in a canine animal, which are not (too) pathogenic to the animal, and preferably for which molecular biological tools are available for their recombination and manipulation. Examples are attenuated or non-pathogenic isolates of bacteria: Ehrlichia, Leptospira or Borrelia; parasites: Leishmania, or Neospora (preferably as in WO 04/026, 903), or even Babesia itself; or viruses: Canine parvovirus, distemper virus, pox virus, hepatitis virus, parainfluenza virus, or rabies virus.

For the construction of an LRCM the well known technique of in vitro homologous recombination can be used to stably introduce a nucleic acid according to the invention into the genome of an LRCM. Alternatively the nucleic acid can also be introduced into an LRCM for transient or episomal expression.

As is well known in the art, an effect of the choice of a certain expression system is the level of post-translational processing of the expressed protein that is applied; e.g. a prokaryotic expression system will not attach any glycosylation signals to the polypeptide produced, whereas insect, yeast or mammalian systems do attach N- and/or O-linked glycosylation, of increasing complexity. The proper choice will be that system giving the best balance of polypeptide amount and immunological effectiveness.

The polypeptides according to the invention, or their fragments, may be modified during or after translation, and this may be done biologically or synthetically. Examples are glycosylation or pegylation. A particular advantageous modification for the invention is the addition of a so-called GPI anchor (Glycosyl-phosphatidylinositol), a well-known and highly immunogenic modification of some expressed parasitic polypeptides.

A further aspect of the invention relates to an isolated antibody that can bind specifically to the polypeptide, or the immunogenic fragment thereof, according to the invention. For the invention, an "antibody" is an immunoglobulin or an immunologically active part thereof, for instance a fragment that still comprises an antigen binding site, such as a single chain antibody or a Fab, Fv, scFv, dAb, or Fd fragment, all well known in the art.

Antibodies are characterised by their specificity, i.e. by the molecule that they bind to with such strength that it can be differentiated from any non-specific or background binding, usually by way of diluting out the specific antibody.

Specific antibodies are commonly produced by (over-)immunizing a donor animal with the target polypeptide, and harvesting the antibodies produced from the animal's serum. Well known donors are rabbits and goats. Another example are chickens which can produce high levels of antibodies in the egg-yolk, so-called IgY. Alternatively, antibodies can be produced in vitro, e.g. via the well known monoclonal antibody technology from immortalized B-lymphocyte cultures (hybridoma cells), for which industrial scale production systems are known. Also antibodies or fragments thereof may themselves be expressed in a recombinant expression system, through expression of the cloned Ig heavy- and/or light chain genes.

Such antibodies can conveniently be used for a variety of applications, particularly diagnostics and vaccinations. Diagnostics are described herein below. The use of antibodies in vaccinations relates to so-called passive vaccines. In the last case, the antibodies are preferably adapted to fit the general characteristics of antibodies from the target; in this case the antibodies would be 'caninised'.

The preferred utility for the CBA polypeptides, fragments, and nucleic acids encoding such polypeptides or fragments is in their medical use, in particular for vaccination.

Therefore in one aspect the invention relates to the polypeptide, or the immunogenic fragment thereof, the nucleotide sequence, the nucleic acid, the live recombinant carrier micro-organism, or the antibody, all according to the invention, or a combination of any of these components, for use in a vaccine for canines against Babesiosis.

In a further aspect the invention relates to a vaccine for canines against Babesiosis, comprising the polypeptide, or the immunogenic fragment thereof, the nucleotide sequence, the nucleic acid, the live recombinant carrier micro-organism, or the antibody, all according to the invention, or a combination of any of these components, and a pharmaceutically acceptable carrier.

Such medical uses according to the invention result in improving the immunity of canines, to achieve the prophylaxis, prevention or amelioration of Babesiosis and/or parasitaemia by Babesia parasites in canines. This is demonstrated on the one hand by the origin of the CBA peptides disclosed herein, namely from SPA which is well known to be immunologically protective. In particular this follows from the details as provided in the examples section herein, in particular the animal experiment and the results of the antibody competition-assay, as demonstrated by AlphaLisa®.

The skilled person can readily observe the difference the vaccine according to the invention makes to a target canine, by monitoring the symptoms of disease normally caused by Babesia infection, especially: anaemia and changes to the packed cell volume or haematocrit, temperature, renal function, behaviour, etc.

Such vaccine efficacy becomes apparent upon comparing a vaccinated and an un-vaccinated target animal. Methods to assess such vaccine efficacy are well known in the art.

For instance the parasitaemia of Babesia parasites in a host can easily be determined by light-microscopic counting of the number of erythrocytes that contain Babesia parasites in a blood-smear, as described by Jarra and Brown for malaria (1985, Parasite Immunol., vol. 7, p. 595-606). For enhanced visibility the sample can be counterstained, for instance with Giemsa stain.

Parasitaemia can then be presented as the percentage of infected-over non-infected erythrocytes, or can be presented as the total number of infected erythrocytes in a fixed number of studied erythrocytes. This in turn can be calculated per day, or as a cumulative total over the duration of the parasitaemia, the so-called 'parasite load'.

For the invention, parasitaemia is expressed as parasite load, wherein the $^{10}$Log value of the number of parasite-infected erythrocytes per $10^5$ erythrocytes in daily blood samples taken from the *vena jugularis* are cumulated over the duration of the time that the parasites can be detected. Commonly *Babesia* parasitaemia occurs between 3 and 14 days post challenge, with a peak between 5 and 10 days post challenge.

Specifically, the vaccine according to the invention is capable of reducing the parasitaemia caused by *B. rossi* infection of a vaccinated target animal by more than 70%. Preferably the reduction of parasitaemia is by 75, 80, 85, 90, 95, 97, or even 100%, in that order of preference. Similarly, the vaccine according to the invention is capable of reducing signs of disease caused by *B. canis* infection by more than 50%, preferably more than 60, 70, 80, 85, 90, 95, 97, or even 100%, in that order of preference.

Alternatively, the symptoms of disease caused by the infection with *Babesia* can be expressed in a clinical score, so that the effect of vaccination on clinical scores of vaccinated and unvaccinated target animals upon infection can than be compared. Tables for rating such clinical scores can be set up by the skilled person, for example as described by Schetters et al., 1994 (Vet. Parasitol., vol. 52, p. 219-233) for the symptoms of *B. canis* infection in dogs.

Preferably the vaccine according to the invention is capable of reducing the clinical scores of vaccinated hosts infected with *Babesia* with 50%, more preferably with 60, 70, 80, 90, or even 100%, in that order of preference.

A further advantageous effect of vaccination as described for the invention, is the prevention or reduction of the spread of *Babesia* infection through the canine population, the so-called horizontal spread of infection. This is because ticks that are as yet uninfected; when feeding on vaccinated canines are less likely to become infected, and thus will not readily spread *Babesia* infection to a further canine. Consequently, this leads to a reduction of the prevalence of *Babesia* in the tick vectors of a certain geographical area, and in turn to less transmission of *Babesia* to new canine hosts. In this embodiment the vaccine works as a transmission-blocking vaccine.

Therefore in a preferred embodiment, the vaccine according to the invention is capable of reducing the prevalence of *Babesia* in the tick vectors of a geographical area.

Methods to determine the prevalence of *Babesia* in tick vectors are well known in the art, for instance as described by Lewis et al. (1996, Vet. Paras., vol. 63, p. 9-16), or by more recent methods using reverse line blotting, or PCR of tick tissue.

For the production and application of the vaccine and medical use according to the invention, the invention in a further aspect relates to a method for the preparation of the vaccine according to the invention, the method comprising the admixing of the polypeptide, or the immunogenic fragment thereof, the nucleotide sequence, the nucleic acid, the live recombinant carrier micro-organism, or the antibody according to the invention, or a combination of any of these components, and a pharmaceutically acceptable carrier.

In an embodiment the method according to the invention also comprises the expression of the nucleotide sequence, or the nucleic acid according to the invention in a recombinant expression system as described above.

In a further aspect the invention relates to the use of the polypeptide, or the immunogenic fragment thereof, the nucleotide sequence, the nucleic acid, the live recombinant carrier micro-organism, or the antibody according to the invention, or a combination of any of these components, for the manufacture of a vaccine against Babesiosis in canines.

In a further aspect the invention relates to a method of vaccination of a canine against Babesiosis, comprising the step of inoculating said canine with a vaccine according to the invention.

The term "vaccine" implies the presence of an immunologically effective amount of the polypeptide, or an immunogenic fragment, according to the invention, and the presence of a pharmaceutically acceptable carrier.

What constitutes an immunologically effective amount for the vaccine according to the invention is dependent on the desired effect and on the specific characteristics of the vaccine that is being used. Determination of the effective amount is well within the skills of the routine practitioner, for instance by monitoring the immunological response following vaccination, or after a challenge infection, e.g. by monitoring the targets' clinical signs of disease, serological parameters, or by re-isolation of the pathogen, and comparing these to responses seen in unvaccinated animals.

In general a vaccine induces an immune response that aids in preventing, ameliorating, reducing sensitivity for, or treatment of a disease or disorder resulting from infection with a micro-organism. The protection is achieved as a result of administering (a composition containing) one ore more antigens derived from that micro-organism, such as an attenuated or killed micro-organism and/or a subunit thereof. This will cause the target animal to show a reduction in the number, or the intensity of clinical signs caused by the micro-organism. This may be the result of a reduced colonization or of a reduced infection rate by the micro-organism, leading to a reduction in the number or the severity of lesions and effects that are caused by the micro-organism or by the target's response thereto.

A "pharmaceutically acceptable carrier" is intended to aid in the effective administration of a compound, without causing (severe) adverse effects to the health of the animal to which it is administered. A pharmaceutically acceptable carrier can for instance be sterile water or a sterile physiological salt solution. In a more complex form the carrier can e.g. be a buffer, which can comprise further additives, such as stabilisers or conservatives. Details and examples are for instance described in well-known handbooks e.g.: such as: "Remington: the science and practice of pharmacy" (2000, Lippincot, USA, ISBN: 683306472), and: "Veterinary vaccinology" (P. Pastoret et al. ed., 1997, Elsevier, Amsterdam, ISBN 0444819681).

In a preferred embodiment, the compounds used for the production of the vaccine according to the invention are serum free (without animal serum); protein free (without animal protein, but may contain other animal derived components), animal compound free (ACF; not containing any component derived from an animal); or even 'chemically defined', in that order of preference.

In a further preferred embodiment the vaccine according to the invention additionally comprises a stabiliser.

Often, a vaccine is mixed with stabilizers, e.g. to protect degradation-prone components from being degraded, to enhance the shelf-life of the vaccine, and/or to improve freeze-drying efficiency. Generally these are large molecules of high molecular weight, such as lipids, carbohydrates, or proteins; for instance milk-powder, gelatine, serum albumin, sorbitol, trehalose, spermidine, Dextrane or polyvinyl pyrrolidone, and buffers, such as alkali metal phosphates.

Preferably the stabiliser is free of compounds of animal origin, or even: chemically defined, as disclosed in WO 2006/094,974.

Also preservatives may be added, such as thimerosal, merthiolate, phenolic compounds, and/or gentamicin.

For reasons of e.g. stability or economy, the antigen according to the invention may be freeze-dried. In general this will enable prolonged storage at temperatures above zero ° C., e.g. at 4° C.

Procedures for freeze-drying are known to persons skilled in the art, and equipment for freeze-drying at different scales is available commercially.

Therefore, in a more preferred embodiment, the vaccines according to the invention are characterised in that said vaccines are in a freeze-dried form.

To reconstitute a freeze-dried vaccine composition, it is suspended in a physiologically acceptable diluent. This is commonly done immediately before use, to ascertain the best quality of the vaccine. The diluent can e.g. be sterile water, or a physiological salt solution. The diluent to be used for reconstituting the vaccine can itself contain additional compounds, such as an adjuvant. In a more complex form it may be suspended in an emulsion as outlined in EP 382.271.

In a variant embodiment of the freeze dried vaccine manufactured according to the use of the invention, the adjuvant for the vaccine is supplied separately from the freeze dried cake comprising the rest of the vaccine, and is preferably comprised in a buffered diluent. In this case, the freeze dried vaccine and the special diluent composition form a kit of parts that together embody the present invention.

Therefore, in a preferred embodiment of the freeze dried vaccine according to the invention, the freeze dried vaccine is comprised in a kit of parts with at least two types of containers, one container comprising the freeze dried vaccine, and one container comprising an aqueous diluent comprising a buffer and a saponin adjuvant.

Preferably the freeze-dried vaccine is in the form as disclosed in EP 799.613.

The vaccine according to the invention may additionally comprise a so-called "vehicle". A vehicle is a compound to which the proteins, protein fragments, nucleic acids or parts thereof, cDNA's, recombinant molecules, live recombinant carriers, and/or host cells according to the invention adhere, without being covalently bound to it. Such vehicles are i.a. bio-microcapsules, micro-alginates, liposomes, macrosols, aluminium-hydroxide, -phosphate, -sulphate or -oxide, silica, Kaolin®, and Bentonite®, all known in the art.

An example is a vehicle in which the antigen is partially embedded in an immune-stimulating complex, the so-called ISCOM® (EP 109.942, EP 180.564, EP 242.380).

In addition, the vaccine according to the invention may comprise one or more suitable surface-active compounds or emulsifiers, e.g. Span® or Tween®.

The age, weight, sex, immunological status, and other parameters of the canines to be vaccinated are not critical, although it is evidently favourable to vaccinate healthy targets, and to vaccinate as early as possible to prevent any field infection. As an infection by Babesia can be established already at very young age, therefore the vaccine according to the invention can be applied within the first 2 weeks after birth, however the presence of maternally derived antibodies in colostrum may need to be factored in for an efficient vaccination at young age.

Target subjects for the vaccine according to the invention are canines that may be healthy or diseased, and may be seropositive or -negative for Babesia parasites or for antibodies to Babesia parasites. The target canine can be of any age at which it is susceptible to the vaccination.

The vaccine according to the invention can equally be used as prophylactic and as therapeutic treatment, and interferes both with the establishment and/or with the progression of a Babesia infection or its clinical signs of disease.

The vaccine according to the invention can effectively serve as a priming vaccination, which can later be followed and amplified by a booster vaccination, for instance with a classical inactivated-adjuvanted vaccine.

The scheme of the application of the vaccine according to the invention to the target canine can be in single or multiple doses, which may be given at the same time or sequentially, in a manner compatible with the dosage and formulation, and in such an amount as will be immunologically effective.

The protocol for the administration of the vaccine according to the invention ideally is integrated into existing vaccination schedules of other canine vaccines.

The vaccines of the invention are advantageously applied in a single yearly dose.

The preparation of a vaccine according to the invention is carried out by means well known to the skilled person.

Such vaccine manufacture will in general comprise the steps of admixing and formulation of the components of the invention with pharmaceutically acceptable excipients, followed by apportionment into appropriate sized containers. The various stages of the manufacturing process will need to be monitored by adequate tests, for instance by immunological tests for the quality and quantity of the antigens; by microbiological tests for sterility and absence of extraneous agents; and ultimately by animal experiments for vaccine efficacy and safety. All these are well known to a skilled person.

A vaccine according to the invention may take any form that is suitable for administration to canine animals, and that matches the desired route of application and the desired effect.

The vaccine according to the invention can be in several forms, e.g.: a liquid, a gel, an ointment, a powder, a tablet, or a capsule, depending on the desired method of application to the target. Preferably the vaccine according to the invention is formulated in a form suitable for injection, thus an injectable liquid such as a suspension, solution, dispersion, or emulsion. Commonly such vaccines are prepared sterile.

Vaccines according to the invention can be administered in amounts containing between 0.1 and 1000 µg of a polypeptide or fragment thereof according to the invention. Smaller or larger doses can in principle be used; preferably between 50 and 250 µg of the polypeptide is used per dose.

Vaccines according to the invention, can be administered in a volume that is consistent with the target canine, for instance, one vaccine dose for a dog can be between 0.5 and 5 ml. Preferably one dose is between 1 and 3 ml.

The vaccine according to the invention can be administered to the canine target according to methods known in the art. For instance by parenteral applications such as through all routes of injection into or through the skin: e.g. intramuscular, intravenous, intraperitoneal, intradermal, submucosal, or subcutaneous. Alternative routes of application that are feasible are by topical application as a drop, spray, gel or ointment to the mucosal epithelium of the eye, nose, mouth, anus, or vagina, or onto the epidermis of the outer skin at any part of the body; by spray as aerosol, or powder. Alternatively, application can be via the alimentary route, by combining with the food, feed or drinking water e.g. as a powder, a liquid, or tablet, or by administration directly into the mouth as a liquid, a gel, a tablet, or a capsule, or to the anus as a suppository.

The preferred application route is by intramuscular or by subcutaneous injection.

It goes without saying that the optimal route of application will depend on the specific vaccine formulation that is used, and on particular characteristics of the target canine.

The vaccine according to the invention is advantageously used as a marker vaccine; a marker vaccine is known as a vaccine that allows the discrimination between vaccinated and field-infected subjects. This is determined e.g. by detection of a vaccine-characteristic antibody panel, that is different from the antibody panel induced by infection with the wild type infectious agent. Such difference is for instance obtained when an immunogenic protein present in or on a wild type micro-organism is not present in the vaccine. This can conveniently be detected by a serological assay such as an ELISA or immunofluorescence assay.

Therefore, in a preferred embodiment, the vaccine according to the invention is a marker vaccine.

It is within reach of a skilled person to further optimise the vaccine of the invention. Generally this involves the fine-tuning of the efficacy of the vaccine, so that it provides sufficient immune-protection. This can be done by adapting the vaccine dose, or by using the vaccine in another form or formulation, or by adapting the other constituents of the vaccine (e.g. the stabiliser or the adjuvant), or by application via a different route.

The vaccine may additionally comprise other compounds, such as an adjuvant, an additional antigen, a cytokine, etc. Alternatively, the vaccine according to the invention can advantageously be combined with a pharmaceutical component such as an antibiotic, a hormone, or an anti-inflammatory drug.

In a preferred embodiment, the vaccine according to the invention is characterised in that it comprises an adjuvant.

An "adjuvant" is a well known vaccine ingredient, which in general is a substance that stimulates the immune response of the target in a non-specific manner. Many different adjuvants are known in the art. Examples of adjuvants are Freund's Complete and -Incomplete adjuvant, vitamin E, non-ionic block polymers and polyamines such as dextransulphate, carbopol and pyran.

Furthermore, peptides such as muramyldipeptides, dimethylglycine, tuftsin, are often used as adjuvant, and mineral oil e.g. Bayol® or Markol®, vegetable oils or emulsions thereof and DiluvacForte® can advantageously be used.

Preferred adjuvant for the vaccine according to the invention is Saponin, more preferably Quil A®. Saponin adjuvant is preferably comprised in the vaccine according to the invention, at a level between 10 and 10.000 µg/ml, more preferably between 100 and 500 µg/ml. Saponin and vaccine components may be combined in an ISCOM® (EP 109.942, EP 180.564, EP 242.380).

It goes without saying that other ways of adjuvating, adding vehicle compounds or diluents, emulsifying or stabilizing a vaccine are also within the scope of the invention. Such additions are for instance described in the well-known handbooks. The vaccine according to the invention can advantageously be combined with another antigen.

Therefore, in a more preferred embodiment the vaccine according to the invention is characterised in that it comprises an additional immunoactive component.

The "additional immunoactive component" may be an antigen, an immune enhancing substance, and/or a vaccine; either of these may comprise an adjuvant.

The additional immunoactive component when in the form of an antigen may consist of any antigenic component of human or veterinary importance. It may for instance comprise a biological or synthetic molecule such as a protein, a carbohydrate, a lipopolysaccharide, a nucleic acid encoding a proteinaceous antigen. Also a host cell comprising such a nucleic acid, or a live recombinant carrier micro-organism containing such a nucleic acid, may be a way to deliver the nucleic acid or the additional immunoactive component. Alternatively it may comprise a fractionated or killed micro-organism such as a parasite, bacterium or virus.

The additional immunoactive component(s) may be in the form of an immune enhancing substance e.g. a chemokine, or an immunostimulatory nucleic acid, e.g. a CpG motif. Alternatively, the vaccine according to the invention, may itself be added to a vaccine.

For instance a vaccine according to the invention can be combined with a preparation of a parasitic subunit vaccine protein, not being a polypeptide according to the invention, to form a combination subunit vaccine against parasitic infection or associated clinical signs of disease.

In a preferred embodiment, the vaccine according to the invention is characterised in that the additional immunoactive component or nucleotide sequence encoding said additional immunoactive component is obtained from a micro-organism infective to canines.

The advantage of such a combination vaccine is that it not only induces an immune response against *Babesia* but also against other (canine) pathogens while only a single handling of the animal for the vaccination is required, thereby preventing needless stress to the target animal, as well as time- and labour costs.

Examples of canine pathogens are: *Ehrlichia canis, Leishmania donovani*-complex, *Neospora caninum, Canine parvovirus, Canine distemper* virus, *Leptospira interrogans* serovar *canicola, icterohaemorrhagiae, pomona, grippotyphosa,* or *bratislava, Canine hepatitis* virus, *Canine parainfluenza* virus, *rabies* virus, *Hepatozoon canis* and *Borrelia burgdorferi*, and species of *Babesia* and *Theileria*.

The polypeptide, nucleotide sequence and the antibodies according to the invention, can advantageously be used for diagnostic purposes.

Therefore a further aspect of the invention relates to a diagnostic test kit comprising the polypeptide, or the immunogenic fragment thereof, the nucleotide sequence, or the antibody, according to the invention.

Commonly such tests are based on Elisa or immunofluorescence protocols.

In an embodiment, the invention relates to a diagnostic test for the detection of a nucleotide sequence from a canine *Babesia*, using a nucleotide sequence according to the invention. The nucleotide sequence is preferably used in a PCR based assay, and has a length of between 10 and 50 nucleotides, preferably between 15 and 30 nucleotides.

In an embodiment the invention relates to a diagnostic test for the detection of antibodies against a canine *Babesia*, wherein said test comprises a polypeptide or an immunogenic fragment thereof, according to the invention.

For instance a CBA polypeptide is coupled to a solid phase carrier, this is incubated with a sample to be tested, is washed, and presence of bound antibodies from the tested sample is detected. The test sample for instance derives from bodily fluids of a canine.

In an embodiment the invention relates to a diagnostic test for the detection of antigenic material from a canine *Babesia*, wherein the test comprises an antibody against a polypeptide (or immunogenic fragment thereof) according to the invention.

For instance antibodies against a CBA polypeptide are coupled to a solid phase carrier, this is incubated with a sample to be tested, is washed, and presence of bound polyprotein from the tested sample is detected. The test sample for instance derives from blood or tissues of a canine. For the invention, the "diagnostic test kit" relates to a kit to perform the diagnostic methods of the invention. The kit comprises one or more of the components of the invention: the polypeptide, or the immunogenic fragment thereof, the nucleotide sequence, or the antibody, in a convenient form and container, optionally with a diluent, a reagent, and/or instructions how to perform the method.

In an embodiment the kit may comprise a container having multiple wells, such as a microtitration plate. The wells of the container may be treated to contain any of the components of the invention, for use in a diagnostic method according to the invention.

The instructions optionally comprised with the diagnostic kit according to the invention, may for example be written on a box containing the constituents of the kit; may be present on a leaflet in that box; or may be viewable on, or downloadable from, an internet website from the distributor of the kit, etc.

For the invention, the diagnostic kit may also be an offer of the mentioned parts (relating to commercial sale), for example on an internet website, for combined use in an assay comprising the methods according to the invention.

The invention will now be further described with reference to the following, non-limiting, examples.

EXAMPLES

Example 1

Preparations

Full-length cDNA of each CBA mRNA was expressed in *E. coli* according to standard procedures and CBA polypeptides were purified for further use and analysis.

Purified CBA-1 was used to generate a hybridoma cell-line according to standard procedures. The cell-line was named 7E6, and it expresses a CBA-1 specific monoclonal antibody.

Example 2

Identification of CBA Shared Epitope and Competition with SPA-Specific Antibodies Polyclonal antibodies were obtained from SPA multiply vaccinated, and subsequently challenged dogs as described before (Schetters et al., 1996, Parasite Immunol., vol. 18, p. 1-6). These antibodies were used in the so-called AlphaLisa® technique (Perkin Elmer) to study common epitopes.

The AlphaLisa technique allows the detection of antigens containing at least two distinct epitopes by virtue of the fact that a donor and acceptor bead each carrying a distinct antibody recognizing a different epitope on the antigen. In the presence of the antigen, the donor and acceptor bead are brought together in close proximity so that energy transfer between the beads may occur. This can be detected with an appropriate detector. In detail: the vaccination-challenge immunoglobulin was biotinylated according to standard procedures. Next this was incubated for 60 minutes with the antigen and the acceptor beads that had been coated with a non-biotinylated vaccination-challenge 1 g. In this mixture, complexes with antigen and biotinylated vaccination-challenge Ig are formed on the acceptor beads. In a second step streptavidin coated donor beads are added, and incubated for 30 minutes, which interact with the biotin groups on the acceptor bead complex. The unique properties of both types of beads allows detection of beads that interact with each other (through the antigen-antibody complexes), which is a measure of the antigen concentration in the sample.

First it was examined whether the recombinant *B. canis* CBA-1 polypeptide is recognized in the AlphaLisa assay, using the polyclonal vaccination-challenge serum. This was to study if CBA-1 presents at least two epitopes that can be recognized by the polyclonal antiserum.

As a negative control in these assays an irrelevant recombinant antigen expressed in a similar way in *E. coli* was used: HSP70 of *Mycobacterium paratuberculosis*.

Positive control and reference material was SPA from a concentrated supernatant from in vitro cultures of the respective parasite species: either *B. canis* or *B. rossi*.

Figure 4:
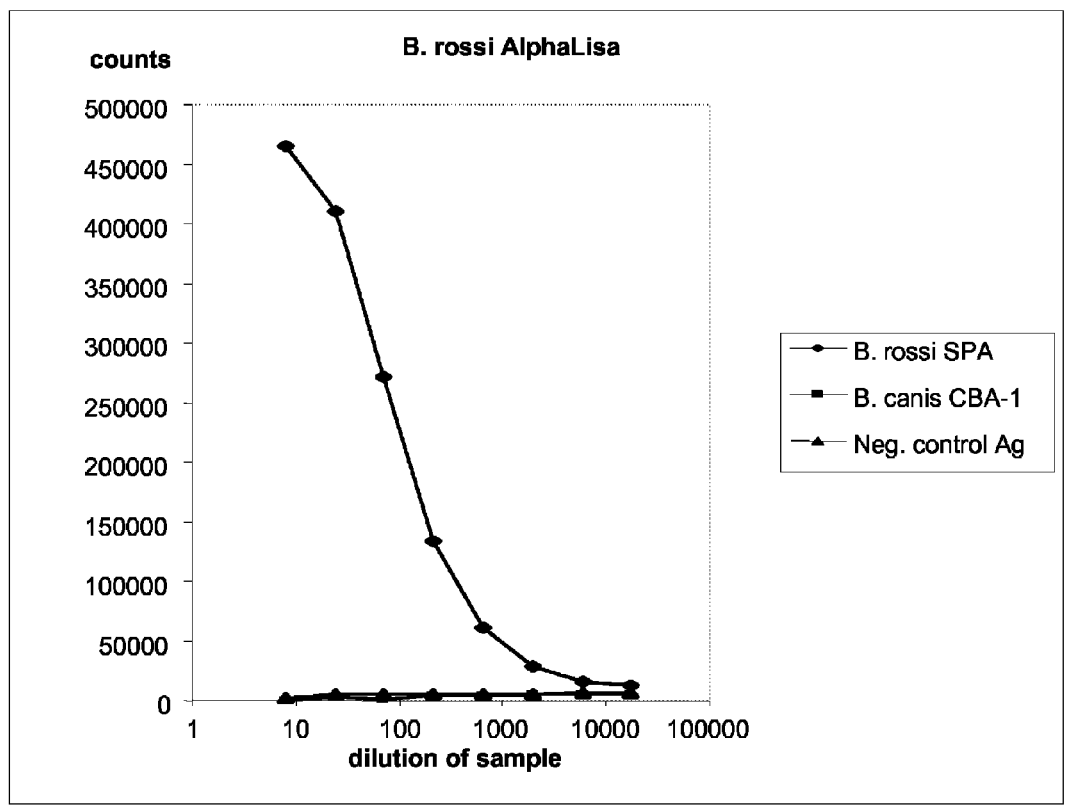

Results showed that the recombinant *B. canis* CBA-1 molecule was undetectable in two separate AlphaLisa assays with either *B. canis* SPA or *B. rossi* SPA polyclonal antibodies. (FIGS. 3 and 4). The positive control sample gave a strong signal in its respective assays.

This shows that the recombinant *B. canis* CBA-1 molecule does not display two or more separate epitopes on a single molecule, which epitopes would be recognised by anti-SPA antibodies. Consequently, the recombinant *B. canis* CBA-1 antigen displays either no epitope at all, or only a single epitope.

The same results are obtained when the *B. rossi* recombinant CBA-2.1 polypeptide is tested in either the *B. canis* or *B. rossi* AlphaLisa assay. This shows that the recombinant *B. rossi* CBA-2.1 polypeptide also does not display two or more separate epitopes on a single molecule. Similarly this means that the recombinant *B. rossi* CBA-2.1 polypeptide displays either no epitope at all, or only a single epitope.

In order to distinguish between these two options, an inhibition AlphaLisa assay was developed, much like the well-known competition Elisa, but employing the dual binding capabilities of the AlphaLisa technology.

The test was set-up to determine if recombinant *B. canis* CBA-1 was capable to compete with the reference SPA antigen for binding with polyclonal antibodies on donor and acceptor beads.

Figure 5:
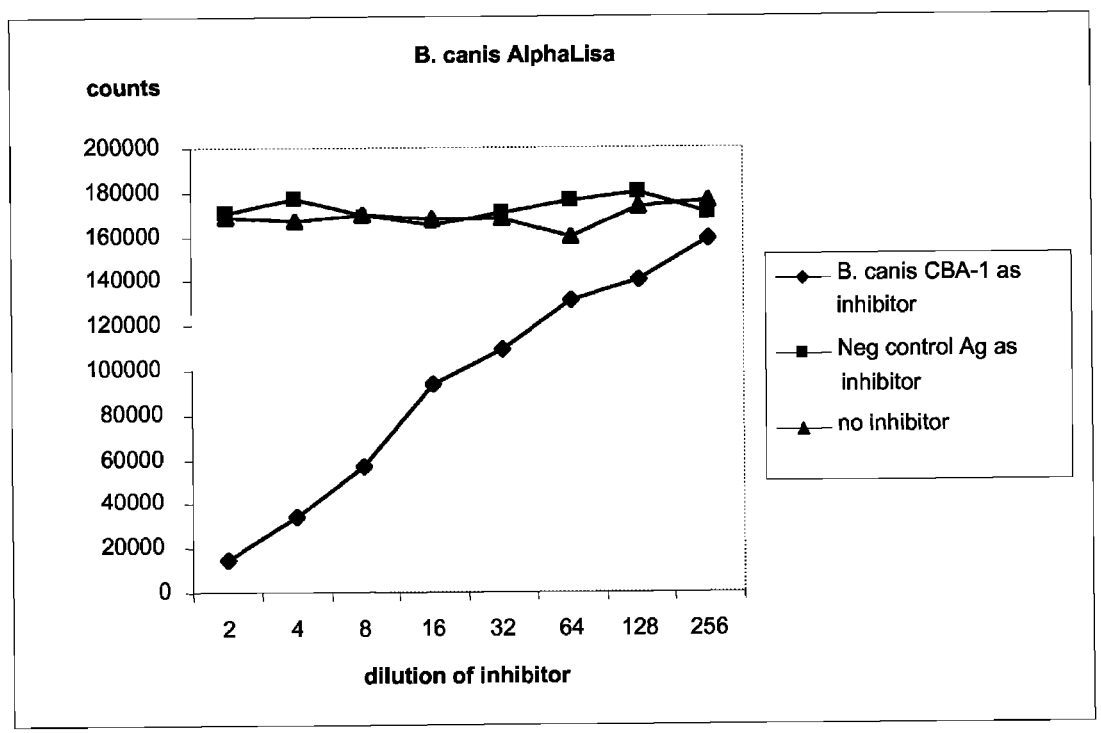
Figure 6:
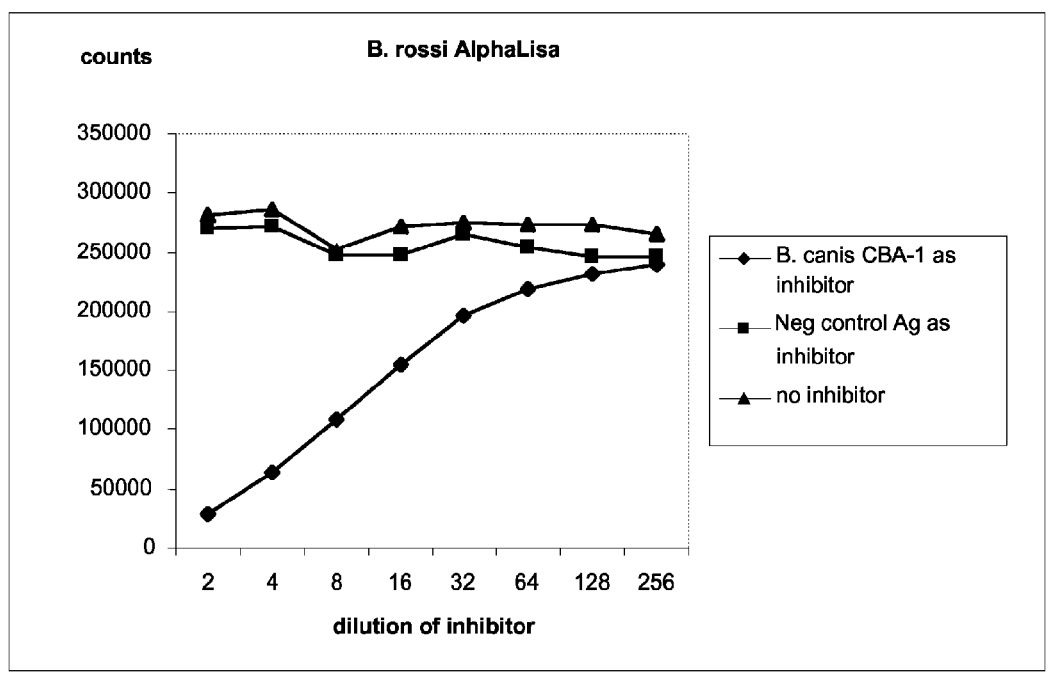

The result was that recombinant *B. canis* CBA-1 polypeptide did indeed inhibit the AlphaLisa signal in both assays, and in fact did so almost quantitatively, see FIGS. 5 and 6.

Conversely, the recombinant *B. rossi* CBA was also able to inhibit the AlphaLisa signal in both assays almost quantitatively (data not shown).

Conclusions:

The CBA-1 polypeptide displays an epitope that is recognised by a vaccination-challenge serum against *B. canis* SPA and by a serum against *B. rossi* SPA. The same is true for *B. rossi* CBA-2.1, and probably also for CBA-2.2.

As determined in AlphaLisa, CBA-1 and CBA-2 that display the epitope are the only (single) antigens recognized in the crude SPA sample of *B. canis* and *B. rossi*, respectively.

Considering that SPA is known to be linked to vaccine protection, and that this vaccine protection is to a large part antibody mediated; therefore the fact that CBA polypeptides can specifically and very effectively compete with the immunoprotective antigens from a SPA sample, means that the CBA polypeptides themselves are immunoprotective antigens.

Also, it is known that *B. canis* SPA in combination with *B. rossi* SPA is effective in heterologous vaccination and protection against *B. rossi*; however, as CBA was not shown to have two recognised epitopes, therefore CBA is shown to express a single cross-protective epitope. Therefore CBA is a heterologous immunoprotective antigen against both *B. rossi* and *B. canis*.

Example 3

CBA Protects Dogs Against Homologous and Heterologous *Babesia* Challenge

Recombinant *Babesia* CBA antigen will be tested for its ability to protect dogs against a homologous challenge infection after priming and booster vaccination. Dogs will be challenged with *B. canis* parasites of strain A to assess the level of protection. The challenge inoculum will be prepared from blood of an infected splenectomised dog. Dogs will then be followed up for a period of 14 days after the challenge infection.

Study Design:

Two groups of 7 dogs/group will be used. Sex and litters will be equally distributed over the two groups.

One group will be vaccinated with 50 µg/dose CBA, a second group will act as a control, and will receive no injections. All antigens will be adjuvated with 250 µg/dose Saponin. Three weeks thereafter, group one will receive a booster vaccination with essentially the same antigen. Weekly serum samples will be taken to determine antibodies against *B. canis* A and *B. rossi* strain antigens using antibody Elisa's. Two weeks after the final vaccination, dogs will be challenged with *B. canis* strain A parasites, which will be obtained from an infected dog. During the post-challenge period animals will be observed daily for clinical signs of Babesiosis. Daily blood samples will be taken to determine packed cell volume and parasitaemia.

Test Materials:

Saponin Supersap® will be obtained from Desert King (Chile). Saponin is prepared with 10 mM Sörenson buffer pH 6.0 in a concentration of 250 µg/ml. The lyophilized antigen is reconstituted in the adjuvant solution. After reconstitution of the antigen, one ml of the solution will represent a single dose.

Beagle dogs of either sex and approximately 5-6 months of age will be used. The dogs will be obtained from a commercial breeder. Only healthy animals will be used. The animals should not have a history of Babesiosis or clinical bacterial infection. Animals will have a unique number tattooed in the ear to allow identification. Additionally, animals will be equipped with a transponder to measure body temperature responses. Dogs will be fed a standard diet, and receive drinking water ad libitum.

Animals will be vaccinated with the test article by subcutaneous injection in the scruff of the neck according to routine procedures. Priming vaccination will be followed by a booster vaccination after three weeks.

At day zero, prior to vaccination, 8 ml blood will be collected of each dog from the *vena jugularis* for the production of negative control serum. Serum will be stored below −15° C. until analysis. From that date on, blood will be collected at weekly intervals for a period of five weeks for the production of serum. Serum will be stored below −15° C. until analysis.

Antibody titres against *B. canis* and *B. rossi* antigens will be determined according to conventional procedures as described in the prior art.

Local reactions at the injection site will be recorded at 24 hour intervals for the duration of the signs, or maximally for 5 days. The nature of the local reaction will be described as (qualitative measure): S=soft; H=hard; O=oedematous; W=warm; P=painful.

A healthy Beagle dog of either sex will be infected with 1 ml of *B. canis* infected blood that was stored as a stabilate in liquid nitrogen. One ampoule of stabilate will be taken from the liquid nitrogen storage and immediately transferred to a liquid nitrogen transport container. The ampoule will immediately be thawed at 30-38° C. just prior to injection in the splenectomized donor dog. The development of parasitaemia in the donor dog will be assessed from blood smears prepared from venous blood collected from the day of infection until the day of patent parasitaemia. Blood samples will be taken from the *vena jugularis* using CPDA tubes (Greiner or comparable) to prevent coagulation. When parasitaemia is patent, blood will be collected (volume is depending from the parasitaemia), and further processed to become the challenge inoculums according to procedures known to the skilled person.

All dogs will be challenged with blood from the infected splenectomised donor dog. Blood will be washed with *Babesia* medium (Schetters et al., 1994, supra). The amount of blood containing $10^6$ parasitized erythrocytes per ml will be injected intravenously in experimental animals (1 ml/dog).

After challenge infection all experimental animals will be examined daily for clinical signs of Babesiosis. Special attention will be given to behaviour, spleen size, size of lymph nodes, colour of the mucous membranes of mouth and eyelid, and the capillary refill time. These parameters will be scored according to the criteria described in Schetters et al. 1994 (supra).

The haematocrit value will be expressed as packed cell volume (PCV) of a sample of venous blood taken from the *vena jugularis* (2 ml heparinised blood/dog). A haematocrit capillary will be filled with heparinised blood and centrifuged in a haematocrit centrifuge (Hettich) for 5 min. at 10.000 rpm. The packed cell volume will be read using a haematocrit reader.

Smears will be prepared from the blood sample that is collected for the determination of the haematocrit blood. Percentage of infected red blood cells will be determined from the blood smears after staining with May-Grünwald/Giemsa solutions.

Plasma will be collected after challenge infection. It will be prepared from the blood sample that is collected for the determination of the haematocrit. The sample will be kept at ambient temperature. Cells will be pelleted by centrifugation (1500×g, 5 min, 4° C.), and the clear plasma is aspirated and stored at −20° C. prior to use.

When indicated after clinical examination, dogs will be treated for Babesiosis by intramuscular injection of imidocarb dipropionate (0.6 ml Carbesia, Schering-Plough Animal Health) for two consecutive days.

Interpretation of Results:

The average body temperature (±standard deviation) will be calculated for each experimental group. Differences will be analysed by ANOVA. P-values <0.05 will be considered statistically significant.

Local reactions will be given a numeric value according to the following table:

| Score | Description | value |
|---|---|---|
| S, H or O | Soft, Hard, Oedematous | 1 |
| W | Warm | 1 |
| P | Painful | 1 |

The score per animal will be summed and the average of each experimental group will be calculated. Differences will be analysed by ANOVA. P-values <0.05 will be considered statistically significant.

The antibody titres against *B. canis* A and *B. rossi* antigens will be measured for each dog. From these antibody titres the potency titre will be calculated.

At least 80% of the animals in the groups should survive until the end of the experiment.

Example 4

CBA-1 Protects Dogs Against Severe *Babesia* Canis Challenge

CBA-1 protein was produced, and a vaccination-challenge experiment in dogs was performed, essentially as described in Example 3. In short:

4.1 Production and Refolding of CBA-1 Protein:

CBA-1 was produced by *E. coli* bacteria, using *E. coli* strain: BL21(DE3), transfected with a pET-101 vector comprising the full length cDNA sequence for CBA-1, with a C-terminal hexaHistidine tag, in a 3-liter fermentor operating in fed-batch mode at 37° C. The base medium was LB with phosphate buffer (6 g/l $Na_2HPO_4$, and 3 g/l $KH_2PO_4$); the feed medium contained 10 fold phosphate buffer, 50% glucose, and 5% yeast extract. The feed pump control was set to maintain the dissolved oxygen level at 40%. After feeding with 50 ml, IPTG was added (to a final concentration of 1 mM) to induce expression, and the culture was maintained for an additional 4 hours before harvesting.

At harvest, 30 g (wet weight) of cell paste was disrupted in a high pressure homogenizer (Emulsiflex™, from Avestin) in PBS at 1200 bar. The resulting lysate was centrifugated (10.000×g for 20 min.), and the pellet was washed 3 times in PBS with 1% Triton-X100®. As the rec. CBA-1 appeared as insoluble material, this was dissolved in a buffer containing 6M Urea, 50 mM $NaH_2PO_4$ and 300 mM KCl, at pH=8. The harvested rec. CBA-1 protein was coupled to a 5 ml HisTrap® column for purification, as well as for refolding to allow the presentation of conformational epitopes, and remove urea while keeping the protein soluble. On-column refolding was applied using 50 column volumes of gradient buffer (509 mM $NaH_2PO_4$, 300 mM KCl, and containing as redox couple 3 mM/0.3 mM oxidized/reduced glutathione). Elution was with a gradient of phosphate-KCl buffer containing up to 400 mM imidazole. Run-off fractions were selected by detection of protein content with UV at 280 nm, and confirmation by SDS-PAGE gel-electrophoresis. The relevant fractions were pooled.

The recombinant CBA-1 protein obtained was 20 ml at 250 µg/ml (approximately 5 mg of total protein) in elution buffer. The purity was better than 85%, as determined by SDS-PAGE and CBB staining.

4.2 Vaccination and Challenge Experiment:

The vaccination-challenge experiment was executed as described in Example 3, except that the vaccination applied was boostered two times, at 3 and at 6 weeks post vaccination, in stead of once. Challenge was at 2 weeks after the last vaccination. Controls were not vaccinated as prior research had shown that vaccination with adjuvant either alone, or mixed with lysed red blood cells, did not interfere with the establishment or the progress of a challenge infection.

4.2.1 Results:

General results: temperature readings were incorporated into the clinical score results. Survival rate was 100% as any dog with a clinical score level of 2 or above was treated by a veterinarian with Carbesia™ (Imidocarb dipropionate) to stop the infection and prevent further illness. Local reactions were seen as transient mild swellings at the injection-site, as expected from the use of saponin as adjuvant.

The most descriptive results of an effective immunisation response against a *Babesia* challenge infection are: the clinical score, the parasite load in blood smears, and the decrease in haematocrit of the animals during the challenge. For the vaccination-challenge experiment using *E. coli* expressed CBA-1 protein, these results are presented in Table 5, and FIGS. 7, 8, and 9.

Table 5 presents the results for these three main parameters, and for comparison displays also the results of earlier studies using the crude SPA based vaccine that is marketed as Nobivac® Piro; the results of which have been published in: Schetters et al., 2006 (Vet. Parasitol., vol. 138, p. 140-146).

TABLE 5

Results of most relevant parameters from vaccination-challenge experiment in dogs.

| ANTIGEN | max. clinical score | parasite load | max. PCV decrease |
|---|---|---|---|
| CBA-1 | 1.3 | 3.5 | 46.6 |
| sem | 0.2 | 0.8 | 3.0 |
| non-vaccinated controls | 2.7 | 7.2 | 57.1 |
| sem | 0.3 | 1.4 | 4.3 |
| Nobivac ® Piro | 2.8 | 8.9* | 54.0 |
| sem | 0.7 | 0.9 | 4.0 |
| non-vaccinated controls | 4.2 | 9.7* | 64.6 |
| sem | 0.9 | 0.8 | 4.9 | sem = standard error of the mean
*= numbers are not significantly different

Figure 7:
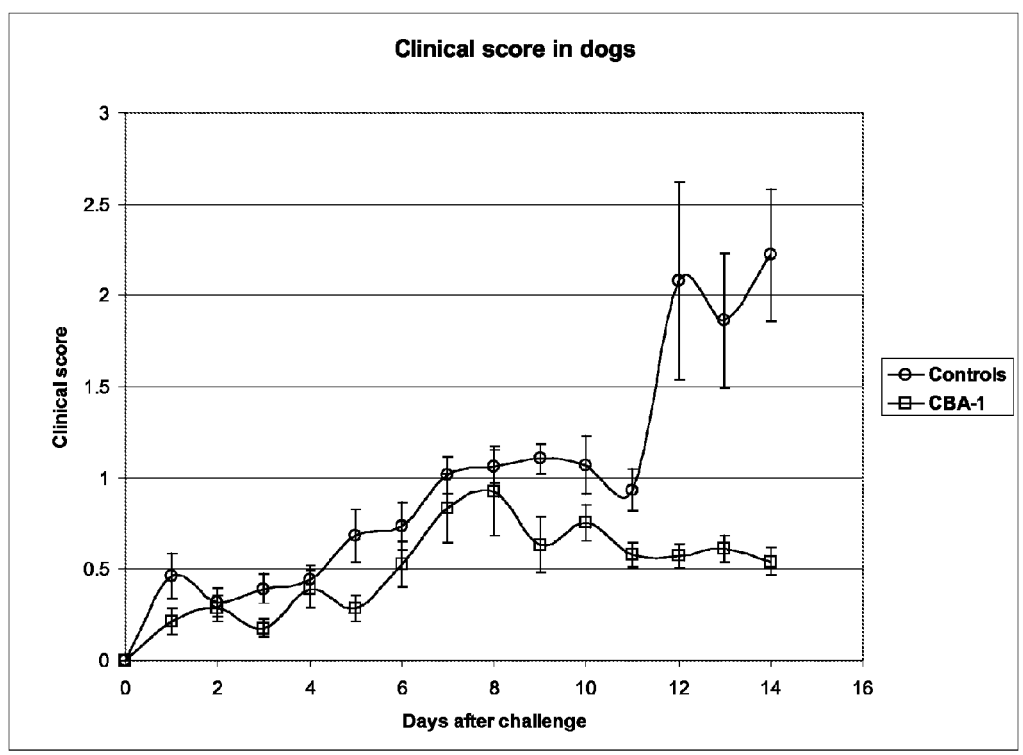

Clinical Score:

The clinical scores were calculated according to the method described previously (Schetters et al. 1994 Vet. Parasitol 52, 219-233). The maximal clinical score value found in the experiment is presented in Table 5, whereas FIG. 7 presents the average values found, per group, per day.

The main symptoms observed in the non-vaccinated controls that caused the relatively high clinical scores, were a paper-white appearance of the mucosae and an increased capillary refill time. It was concluded that CBA-1 vaccination resulted in a significant reduction of clinical score after challenge.

Parasite Load:

The parasite load was calculated as the sum of the daily 10 Log-parasitaemia values; the value at day 14 after challenge (the end of the experiment) is presented in Table 5.

The results show a significant reduction in parasite load in the CBA-1 vaccinated dogs. This had not previously been possible using a crude SPA type vaccine, and this adds considerably to a reduction of the symptoms of disease, and of the time to recovery. Also this serves an important function in the reduction of the spread of the disease to ticks and thus to other dogs in the environment. Results are presented in FIG. 8.

Packed Cell Volume:

PCV values represent the group averages, that are expressed as percentage values relative to those at day 0 (before challenge). The maximal decrease in PCV is presented in Table 5, as not all dogs showed the largest drop in PCV on the same day.

CBA-1 vaccination significantly reduced a decrease of haematocrit resulting from *B. canis* challenge infection. Results are presented in FIG. 9.

Figure 8:
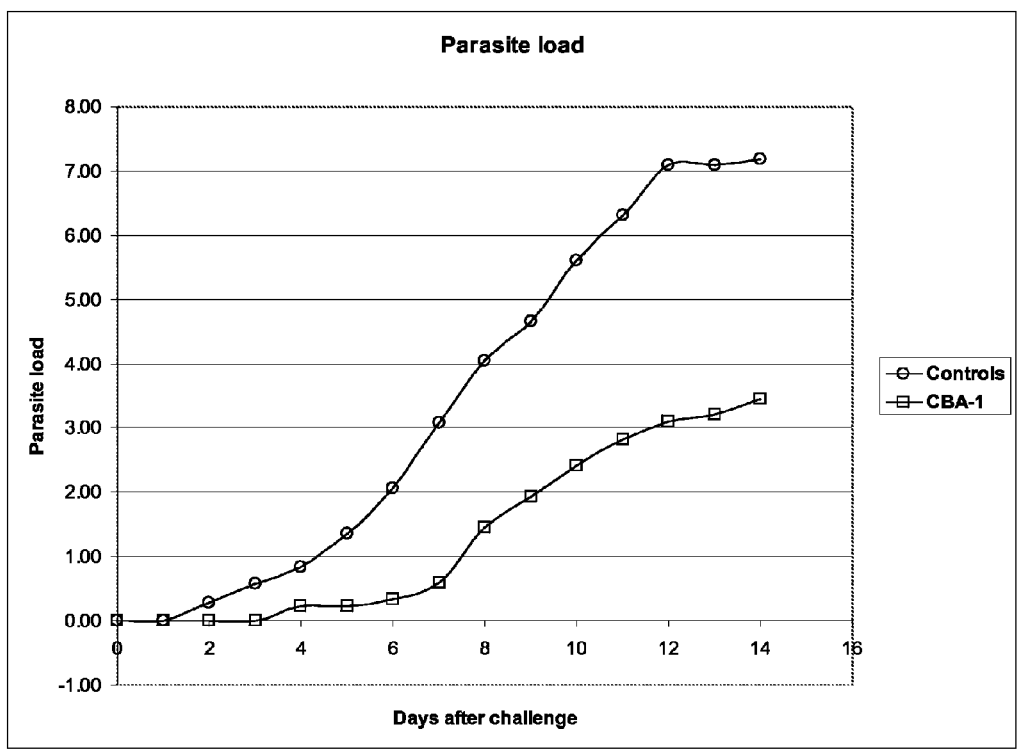
Figure 9:
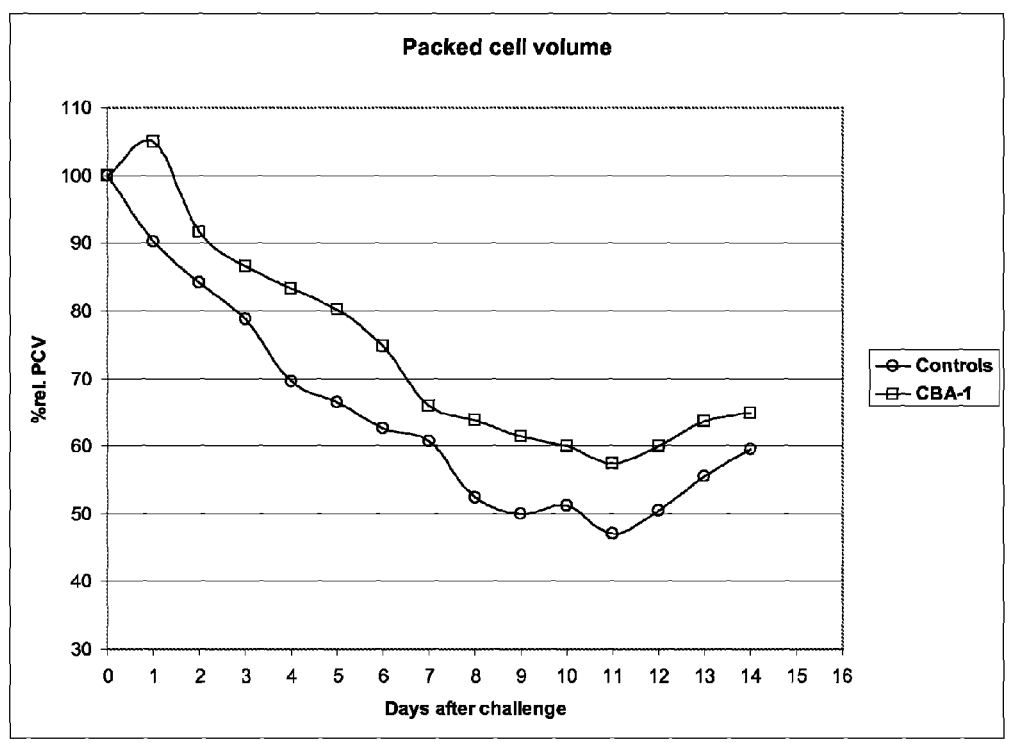

4.3 Conclusions:

As presented in Table 5 and FIGS. 7-9: a vaccination with recombinant expressed CBA-1 protein was able to provide dogs with a significant level of immune protection against both the infection with *Babesia* canis parasites, as well as against the symptoms of the disease this causes. This protection considerably outperformed the currently available commercial canine *Babesia* vaccine.

LEGEND TO THE FIGURES

FIG. 1: Amino acid sequence alignment of CBA polypeptides from *Babesia canis* and *Babesia rossi*. The two characterising regions are boxed, and the putative signal sequence is indicated by a double arrow.

FIG. 2: Nucleotide sequence alignment of CBA-1 mRNA (in cDNA format; SEQ ID NO: 9) and the CBA-1 gene from the genome of *B. canis* (SEQ ID NO: 12).

FIG. 3: Detection of recombinant *B. canis* CBA-1 molecule by AlphaLisa. Detection was performed using the *B. canis* SPA specific polyclonal antibodies.

FIG. 4: Detection of recombinant *B. rossi* CBA-2 molecule by AlphaLisa. Detection was performed using the *B. rossi* SPA specific polyclonal antibodies.

FIG. 5: Detection by inhibition AlphaLisa, of inhibition by recombinant *B. canis* CBA-1 polypeptide of the binding of *B. canis* SPA specific polyclonal antibodies to *B. canis* SPA reference antigen.

FIG. 6: Detection by inhibition AlphaLisa, of inhibition by recombinant *B. canis* CBA-1 polypeptide of the binding of *B. rossi* SPA specific polyclonal antibodies to *B. rossi* SPA reference antigen.

FIG. 7: Average clinical score results per group per day (post challenge), with standard error of mean, from the vaccination-challenge experiment in dogs.

FIG. 8: Parasite load results from vaccination-challenge experiment.

FIG. 9: Haematocrit results (as packed cell volume, in % relative to day 0 [before challenge]) from vaccination-challenge experiment.

The invention claimed is:

1. An isolated nucleic acid comprising a nucleotide sequence encoding a polypeptide or an immunogenic fragment thereof that is at least 8 amino acids in length; wherein said polypeptide comprises an amino acid sequence having a sequence identity selected from the group consisting of greater than 76% with the amino acid sequence of SEQ ID NO: 1, greater than 68% with the amino acid sequence of SEQ ID NO: 3, or greater than 76% with the amino acid sequence of SEQ ID NO: 1 and greater than 68% with the amino acid sequence of SEQ ID NO: 3; wherein said polypeptide and said immunogenic fragment thereof individually induce an immune response against a canine *Babesia* parasite; wherein said nucleotide sequence is under the control of a functionally linked heterologous promoter and does not comprise an intron.

2. The isolated nucleic acid of claim 1, wherein the polypeptide comprises an amino acid sequence comprising the amino acid sequence of SEQ ID NO: 1.

3. The isolated nucleic acid of claim 1, wherein the polypeptide comprises an amino acid sequence comprising the amino acid sequence of SEQ ID NO: 3.

4. A vaccine for canines against Babesiosis, comprising the nucleic acid of claim 1, and a pharmaceutically acceptable carrier.

5. A diagnostic test kit comprising the nucleic acid of claim 1.

6. A method for the preparation of a vaccine for canines against Babesiosis, said method comprising expressing the nucleic acid of claim 1 in a recombinant expression system admixing the resulting expressed product with a pharmaceutically acceptable carrier.

* * * * *

```
                        SEQUENCE LISTING

<160> NUMBER OF SEQ ID NOS: 15

<210> SEQ ID NO 1
<211> LENGTH: 21
<212> TYPE: PRT
<213> ORGANISM: Babesia rossi

<400> SEQUENCE: 1

Met Leu Leu Ser Asn Val Ser Phe Pro Gln Pro Val Ser Ser Val Lys
1               5                   10                  15

Leu Leu Glu Glu Tyr
            20

<210> SEQ ID NO 2
<211> LENGTH: 21
<212> TYPE: PRT
<213> ORGANISM: Babesia canis

<400> SEQUENCE: 2

Ile Leu Leu Ser Asn Val Glu Phe His Thr Pro Val Ser Ser Val Lys
1               5                   10                  15

Leu Leu Lys Glu Tyr
            20

<210> SEQ ID NO 3
<211> LENGTH: 19
<212> TYPE: PRT
<213> ORGANISM: Babesia rossi

<400> SEQUENCE: 3

Val Leu Met Val Leu Thr Lys Cys Asn Leu Lys Met His Val Thr Glu
1               5                   10                  15

Glu Gln Leu

<210> SEQ ID NO 4
<211> LENGTH: 19
<212> TYPE: PRT
```

<213> ORGANISM: Babesia rossi

<400> SEQUENCE: 4

```
Phe Leu Met Val Leu Thr Lys Cys Asp Leu Met Met Ala Ile Pro Glu
1               5                   10                  15

Glu Gln Leu
```

<210> SEQ ID NO 5
<211> LENGTH: 19
<212> TYPE: PRT
<213> ORGANISM: Babesia canis

<400> SEQUENCE: 5

```
Val Leu Met Ile Leu Thr Lys Cys Asp Leu Lys Ala Glu Val Thr Glu
1               5                   10                  15

Glu Gln Ile
```

<210> SEQ ID NO 6
<211> LENGTH: 321
<212> TYPE: PRT
<213> ORGANISM: Babesia canis

<400> SEQUENCE: 6

```
Met Met Leu Leu Phe Ala Leu Ser Thr Leu Val Thr Phe Ala Phe Cys
1               5                   10                  15

Asp Gly Glu Asn Thr Ile Leu Leu Ser Asn Val Glu Phe His Thr Pro
            20                  25                  30

Val Ser Ser Val Lys Leu Leu Lys Glu Tyr Ser Ser Asn Gln Glu Ser
        35                  40                  45

Met Ala Val Ile Met Met Leu Thr Glu Met Pro Asn Thr Ser Gly Lys
    50                  55                  60

Leu Thr Asp Gly Lys Val His Val Ala Asn Asp Asn Val Lys Cys Ala
65                  70                  75                  80

Asp Leu Ala Leu Ala Tyr Gln Glu Leu Lys Lys Ala Gly Lys Val Thr
                85                  90                  95

Ser Trp Ser Pro Thr Asp Asp Asn Asp Lys Val Val Pro His Gly Ile
            100                 105                 110

Trp Phe Ile Glu Gly Val Tyr Glu Thr Asp Lys Met Phe Glu Val Tyr
        115                 120                 125

Lys Thr Leu Thr Asp Pro Glu Asp Pro Ser Glu Val Thr Arg Leu Thr
    130                 135                 140

Thr Val Ser Gly Ala Ser Gly Ser Ala Gln Ser Gln Pro Ala Gly Thr
145                 150                 155                 160

Thr Asp Gly Val Ser Gly Ser Ala Ala Ser Ala Ser Gly Ser Ser Gly
                165                 170                 175

Ser Thr Thr Ser His Ser Thr Thr Ala Thr Thr Ser Ser Thr Ser Thr
            180                 185                 190

Val Ser Thr Ser Ser Ser Gly Ala Ser Thr Ser Ser Ser Thr Asp Gln
        195                 200                 205

Ala Ser Met Leu Thr Thr Gln Thr Ser Tyr Ser Ala Gly Ser Ser Val
    210                 215                 220

His Lys Ser Ala Val Val Ala Pro Thr Gln Ser Thr Thr Pro Asp Asn
225                 230                 235                 240

Ala Glu Ser Gly Ala Lys Gln Ser Lys Ala Ala Val Gln Glu Pro Lys
                245                 250                 255

Asn Val Leu Met Ile Leu Thr Lys Cys Asp Leu Lys Ala Glu Val Thr
```

```
            260                 265                 270
Glu Glu Gln Ile Arg Ser Gln Gly Asn Pro Glu Ser Asn Gly Ser Ser
            275                 280                 285

Ser Glu Pro Thr Ala Ala Ser Pro Lys Leu Thr Thr Ala Ala Ser Gly
    290                 295                 300

Phe Thr Ala Ala Ile Thr Pro Leu Phe Met Val Pro Leu Met Phe Phe
305                 310                 315                 320

Ala

<210> SEQ ID NO 7
<211> LENGTH: 278
<212> TYPE: PRT
<213> ORGANISM: Babesia rossi

<400> SEQUENCE: 7

Met Met Leu Leu Phe Ala Phe Ser Ser Leu Leu Ala Val Ala Ser Cys
1               5                   10                  15

Thr Asp Phe Asn Thr Met Leu Leu Ser Asn Val Ser Phe Pro Gln Pro
            20                  25                  30

Val Ser Ser Val Lys Leu Leu Glu Glu Tyr Ala Lys Tyr Gln Lys Gly
        35                  40                  45

Tyr Val Leu Tyr Phe Gln Met Arg Asp Asp Leu Pro Lys Lys Glu Asp
    50                  55                  60

Thr Glu Arg Phe Ser Gln Tyr Val Gln Leu Glu Asn Ala Glu Cys Thr
65                  70                  75                  80

Asp Leu Ala Ala Ile Tyr Asn Ile Met Gln Arg Glu Gly Arg Ile Phe
                85                  90                  95

Glu Tyr Lys His Glu Ser Glu Leu Pro Asp Tyr Pro Glu Gly Leu Trp
            100                 105                 110

Leu Leu Asp Ala Gln Asp Lys Glu Glu Ile Leu His Thr Phe Glu
        115                 120                 125

Thr Thr Leu Pro Pro Thr Ser Thr Asn Gly Asn Glu His Ala Asp Lys
    130                 135                 140

Thr Arg Glu Ala Pro Lys Pro Arg Pro Asp Ala Pro Ala Ala Ser Asp
145                 150                 155                 160

Thr Gln Arg Ala Gln Asp Asn Gln Glu Lys Thr Pro Thr Glu Ser Ser
                165                 170                 175

Thr Gly Ser Arg Asp Thr Val Gln Pro Gln Thr Ala Pro Ala Thr Ser
            180                 185                 190

Asn Ala Val Thr Gly Thr Ser Ser Thr Thr Ser Ser Val Gln Ser Gln
        195                 200                 205

Ala Val Leu Gly Asn Ser Glu Ala Thr Thr Gly Thr Gln Gln Ser Ala
    210                 215                 220

Glu Asn Val Lys Val Leu Met Val Leu Thr Lys Cys Asn Leu Lys Met
225                 230                 235                 240

His Val Thr Glu Glu Gln Leu Ser Lys His Ser Asn Ile Pro Arg Lys
                245                 250                 255

His Gly Ser Gly Phe Thr Pro Ala Ile Ala Phe Thr Ser Leu Leu Pro
            260                 265                 270

Phe Leu Leu Met Met Ser
        275

<210> SEQ ID NO 8
<211> LENGTH: 274
<212> TYPE: PRT
```

<213> ORGANISM: Babesia rossi

<400> SEQUENCE: 8

Met Met Leu Leu Phe Ala Phe Ser Ser Leu Le

```
actgataaga tgttcgaggt ttacaagacc ctgaccgatc ctgaggaccc aagcgaagtt      420
actcgcttga caactgtttc tggtgcttcc ggatctgctc aaagccagcc tgctggtact      480
actgatggtg tctcgggtag cgctgctagt gcctctggtt cctctggttc cactacttcc      540
cattctacta ccgctactac cagctccact agtaccgttt ctacttcctc ttctggggct      600
tctacttcta gttctactga ccaggcatcc atgcttacca cccaaacatc ctacagtgca      660
ggatctagcg ttcataaaag cgctgtggtt gctcccactc agagtaccac tcctgataat      720
gctgaatctg gcgcaaagca aagcaaagct gcggttcagg aacctaagaa tgttttgatg      780
attctgacca agtgtgatct taaggccgaa gttaccgagg aacagataag aagccaagga      840
aacccagaaa gcaatgggtc ttcttctgaa cccactgctg cttctcctaa acttactacc      900
gctgcttctg gattcactgc cgccattacc cccttgttca tggtcccact catgttttc       960 gcctaa                                                                 966
```

<210> SEQ ID NO 10
<211> LENGTH: 837
<212> TYPE: DNA
<213> ORGANISM: Babesia rossi
<220> FEATURE:
<221> NAME/KEY: mRNA
<222> LOCATION: (1)..(837)

<400> SEQUENCE: 10
atgatgttac tattcgcttt ctcttctctt ctcgcagtgg cctcgtgcac tgattttaac 60
accatgttat tgtccaatgt gagctttcct cagccggttt cgagtgtaaa actacttgaa 120
gaatatgcta aatatcagaa gggttatgtg ttgtatttcc aaatgcgtga tgatttgcca 180
aagaaagagg atactgagag gtttagtcaa tatgttcaac tggagaacgc cgaatgtact 240
gacttggctg ctatctataa tattatgcaa cgtgagggta gaatatttga atacaagcat 300
gaaagcgaac ttcctgatta tcctgaaggc ctgtggttgt tggatgccca ggatgataag 360
gaagaaattc tccacacctt tgagactaca ctccccccta cctctacaaa tggtaatgaa 420
cacgctgata agactagaga ggcacctaag ccaagaccag atgctccagc tgcttctgat 480
acccaacgtg cccaagacaa tcaggaaaag acacccactg agtcgtcaac aggttctcga 540
gacactgttc aacctcaaac tgcccctgca acttcaaacg cagtaactgg tacgtcatca 600
acgacatcaa gtgtgcagag ccaagctgta ttagggaact ctgaagctac tacagggact 660
cagcaatcag ctgaaaatgt taaggtttta atggttctga cgaagtgcaa ccttaaaatg 720
catgttactg aggaacagtt gagcaagcac agcaacatac cccgtaagca tggatcagga 780
ttcactccgg ctattgcatt tacctctctt ctaccattcc tcttgatgat gtcctaa 837

<210> SEQ ID NO 11
<211> LENGTH: 825
<212> TYPE: DNA
<213> ORGANISM: Babesia rossi
<220> FEATURE:
<221> NAME/KEY: mRNA
<222> LOCATION: (1)..(825)

<400> SEQUENCE: 11
atgatgttac tattcgcttt ctcttctctt ctcgcagtgg cctcgtgcac tgattttaac 60
accatgttat tgtccaatgt gagctttcct cagccggttt cgagtgtaaa actacttgaa 120
gaatatgcta aggatgataa ggttacagtt atatttagtg ttttagatac cttgccaacg 180

```
gatgaagcca atggaactag atattccaaa tataaggcag acgataatga taaatgtgtt      240
gatcttgcgc ttgtctttca agagctgcag aagaaaggcc ttgtaaagga atttggtaat      300
gaagatactc caccagaaga agtgaatgga ctatggctaa tgagagggaa acatgctgga      360
cacaacatgc ttgaggtttt tgagacgtta gtaaacccga gacgtggttt agaggatctt      420
ccagttaccc caaaatctgc agaggggcga cgtgaagctg tatcccggag taccgcggaa      480
aatcaggctg ggacaaatgg agagagtggg tcctctcaaa ctgcatccaa tgcgggtaca      540
agtcaggtaa ctgctgctag agtatcaggt gtacaagcac aatccgtagc cgcgggcacg      600
aatggaccac agaatgttag ggaggatact gtccccgctc ctgaagcagt tcctagcaat      660
caggatatga agtttctaat ggttctgact aagtgtgatc ttatgatggc aattcctgag      720
gaacagttga gcgggcccaa aaacatgagg gagaaccagg aatcaggatt cactccggct      780
attgcattta cctctcttct accattcctc ttgatgatgt cataa                     825

<210> SEQ ID NO 12
<211> LENGTH: 1143
<212> TYPE: DNA
<213> ORGANISM: Babesia canis
<220> FEATURE:
<221> NAME/KEY: gene
<222> LOCATION: (1)..(1143)
<220> FEATURE:
<221> NAME/KEY: Intron
<222> LOCATION: (170)..(203)
<220> FEATURE:
<221> NAME/KEY: Intron
<222> LOCATION: (408)..(550)

<400> SEQUENCE: 12
atgatgctgc tcttcgcctt gtctactctt gtcaccttcg ccttctgcga tggtgaaaac       60
actatacttt tatccaatgt agaattccat actccagtat ccagtgtaaa gctgcttaaa      120
gaatacagta gcaatcagga atcaatggcc gttattatga tgctaaccgg taggaaatta      180
tatgcataat tcataattcg cagaaatgcc aaacacatca ggaaagctta ccgatggcaa      240
agttcatgtg ccaatgata acgttaaatg tgctgatttg ctctggctt atcaagaact        300 caaaaaggcc ggcaaggtga catcatggag tccaactgat gacaacgata aggtggtacc      360
tcatggaatc tggttcatag agggcgtcta tgagactgat aagatgtgta agtagatgtg      420
tttatcaacc gtattgggt atactataca attattcagt tgctatatga agtttctggt       480
ttaataattg tgccatgtcc acgccatttg cactattagc attaattaat cgttcctgat      540
gtgttttcag tcgaggttta caagaccctg accgatcctg aggacccaag cgaagttact      600
cgcttgacaa ctgtttctgg tgcttccgga tctgctcaaa gccagcctgc tggtactact      660
gatggtgtct cgggtagcgc tgctagtgcc tctggttcct ctggttccac tacttcccat      720
tctactaccg ctactaccag ctccactagt accgtttcta cttcctcttc tggggcttct      780
acttctagtt ctactgacca ggcatccatg cttaccaccc aaacatccta cagtgcagga      840
tctagcgttc ataaaagcgc tgtggttgct cccactcaga gtaccactcc tgataatgct      900
gaatctggcg caaagcaaag caaagctgcg gttcaggaac taagaatgt tttgatgatt       960 ctgaccaagt gtgatcttaa ggccgaagtt accgaggaac agataagaag ccaaggaaac     1020
ccagaaagca atgggtcttc ttctgaaccc actgctgctt ctcctaaact tactaccgct     1080
gcttctggat tcactgccgc cattaccccc ttgttcatgg tcccactcat gttttttcgcc   1140 taa                                                                   1143
```

<210> SEQ ID NO 13
<211> LENGTH: 1036
<212> TYPE: DNA
<213> ORGANISM: Babesia rossi
<220> FEATURE:
<221> NAME/KEY: gene
<222> LOCATION: (1)..(1036)
<220> FEATURE:
<221> NAME/KEY: Intron
<222> LOCATION: (173)..(207)
<220> FEATURE:
<221> NAME/KEY: Intron
<222> LOCATION: (406)..(569)

<400> SEQUENCE: 13
atgatgttac tattcgcttt ctcttctctt ctcgcagtgg cctcgtgcac tgattttaac 60
accatgttat tgtccaatgt gagctttcct cagccggttt cgagtgtaaa actacttgaa 120
gaatatgcta aatatcagaa gggttatgtg ttgtatttcc aaatgcgtga tggtacgtcg 180
acattttcag ttatcattat gtgacagatt tgccaaagaa agaggatact gagaggttta 240
gtcaatatgt tcaactggag aacgccgaat gtactgactt ggctgctatc tataatatta 300
tgcaacgtga gggtagaata tttgaataca agcatgaaag cgaacttcct gattatcctg 360
aaggcctgtg gttgttggat gcccaggatg ataaggaaga aattcgtaag tttctgcatt 420
cagcaataca atctgcttaa caatttatac tcatccgtct tgtacattat ttgactgtgt 480
taatctatct tgttgttgat tcttttgtat taattgaaca aatttgtgtc aaaggaatat 540
tataatacac tcaccttata taattgtagt ccacaccttt gagactacac tccccctac 600 ctctacaaat ggtaatgaac acgctgataa gactagagag gcacctaagc caagaccaga 660
tgctccagct gcttctgata cccaacgtgc ccaagacaat caggaaaaga cacccactga 720
gtcgtcaaca ggttctcgag acactgttca acctcaaact gcccctgcaa cttcaaacgc 780
agtaactggt acgtcatcaa cgacatcaag tgtgcagagc caagctgtat tagggaactc 840
tgaagctact acagggactc agcaatcagc tgaaaatgtt aaggttttaa tggttctgac 900
gaagtgcaac cttaaaatgc atgttactga ggaacagttg agcaagcaca gcaacatacc 960
ccgtaagcat ggatcaggat tcactccggc tattgcattt acctctcttc taccattcct 1020
cttgatgatg tcctaa 1036

<210> SEQ ID NO 14
<211> LENGTH: 1007
<212> TYPE: DNA
<213> ORGANISM: Babesia rossi
<220> FEATURE:
<221> NAME/KEY: gene
<222> LOCATION: (1)..(1007)
<220> FEATURE:
<221> NAME/KEY: Intron
<222> LOCATION: (170)..(204)
<220> FEATURE:
<221> NAME/KEY: Intron
<222> LOCATION: (406)..(552)

<400> SEQUENCE: 14
atgatgttac tattcgcttt ctcttctctt ctcgcagtgg cctcgtgcac tgattttaac 60
accatgttat tgtccaatgt gagctttcct cagccggttt cgagtgtaaa actacttgaa 120
gaatatgcta aggatgataa ggttacagtt atatttagtg ttttagatag taagttgata 180
taatacgttg atattattgc acagccttgc caacggatga agccaatgga actagatatt 240
ccaaatataa ggcagacgat aatgataaat gtgttgatct tgcgcttgtc tttcaagagc 300

```
tgcagaagaa aggccttgta aaggaatttg gtaatgaaga tactccacca gaagaagtga      360
atggactatg gctaatgaga gggaaacatg ctggacacaa catgcgtatg tttcttagcg      420
tatactgtct agttttgttt cctatcagtt ataaattatt ctcattttc ggagtcatct       480 tcttaaccca ttttatttag tacgcgcaag tgattcataa atattattag tgcccttat      540 atatgtttat agttgaggtt tttgagacgt tagtaaaccc gagacgtggt ttagaggatc      600
ttccagttac cccaaaatct gcagaggggc gacgtgaagc tgtatcccgg agtaccgcgg      660
aaaatcaggc tgggacaaat ggagagagtg ggtcctctca aactgcatcc aatgcgggta      720
caagtcaggt aactgctgct agagtatcag gtgtacaagc acaatccgta gccgcgggca      780
cgaatggacc acagaatgtt agggaggata ctgtccccgc tcctgaagca gttcctagca      840
atcaggatat gaagtttcta atggttctga ctaagtgtga tcttatgatg gcaattcctg      900
aggaacagtt gagcgggccc aaaaacatga gggagaacca ggaatcagga ttcactccgg      960
ctattgcatt tacctctctt ctaccattcc tcttgatgat gtcataa                   1007
```

<210> SEQ ID NO 15
<211> LENGTH: 8
<212> TYPE: PRT
<213> ORGANISM: Babesia rossi

<400> SEQUENCE: 15

```
Pro Val Ser Ser Val Lys Leu Leu
1               5
```